US008664392B2

(12) United States Patent
Rajagopalan et al.

(10) Patent No.: US 8,664,392 B2
(45) Date of Patent: Mar. 4, 2014

(54) PYRAZINE DERIVATIVES FOR BIOCONJUGATION

(75) Inventors: Raghavan Rajagopalan, St. Peters, MO (US); Richard B. Dorshow, Saint Charles, MO (US)

(73) Assignee: MediBeacon, LLC, St. Louis, MO (US)

( * ) Notice: Subject to any disclaimer, the term of this patent is extended or adjusted under 35 U.S.C. 154(b) by 0 days.

(21) Appl. No.: 13/344,930

(22) Filed: Jan. 6, 2012

(65) Prior Publication Data

US 2012/0134930 A1   May 31, 2012

Related U.S. Application Data

(63) Continuation-in-part of application No. 12/281,338, filed as application No. PCT/US2007/006211 on Mar. 9, 2007, now abandoned, application No. 13/344,930, which is a continuation-in-part of application No. 13/343,231, filed on Jan. 4, 2012, which is a continuation of application No. 11/995,223, filed as application No. PCT/US2007/014370 on Jun. 20, 2007, now Pat. No. 8,115,000, which is a continuation-in-part of application No. 11/721,186, filed as application No. PCT/US2005/046732 on Dec. 22, 2005.

(60) Provisional application No. 60/781,530, filed on Mar. 10, 2006, provisional application No. 60/815,712, filed on Jun. 22, 2006, provisional application No. 60/638,611, filed on Dec. 23, 2004.

(51) Int. Cl.
C07D 241/02 (2006.01)
A61K 31/497 (2006.01)
A61K 31/4965 (2006.01)

(52) U.S. Cl.
USPC .... 544/406; 544/407; 514/252.1; 514/255.06

(58) Field of Classification Search
USPC ............... 544/406, 407; 514/252.1, 255.06
See application file for complete search history.

(56) References Cited

U.S. PATENT DOCUMENTS

| | | | |
|---|---|---|---|
| 3,808,209 A | 4/1974 | Donald | |
| 3,814,757 A | 6/1974 | Donald | |
| 3,948,895 A | 4/1976 | Donald | |
| 4,517,186 A | 5/1985 | Johnston | |
| 5,395,619 A | 3/1995 | Zalipsky et al. | |
| 5,631,018 A | 5/1997 | Zalipsky et al. | |
| 5,714,342 A | 2/1998 | Komoriya et al. | |
| 6,258,378 B1 | 7/2001 | Schneider et al. | |
| 6,277,403 B1 | 8/2001 | Mendez et al. | |
| 6,406,713 B1 | 6/2002 | Janoff et al. | |
| 6,440,389 B1 | 8/2002 | Rabito | |
| 6,610,322 B1 | 8/2003 | Keller et al. | |
| 2004/0081622 A1 | 4/2004 | Achilefu et al. | |
| 2011/0250139 A1 * | 10/2011 | Poreddy et al. | 424/9.1 |

FOREIGN PATENT DOCUMENTS

| | | |
|---|---|---|
| CA | 2340250 | 2/2000 |
| DE | 10222738 | 11/2003 |
| EP | 0402472 | 12/1990 |
| GB | 2370581 | 7/2002 |
| JP | 2017163 | 1/1990 |
| JP | 249775 | 2/1990 |
| JP | 4112877 | 4/1992 |
| JP | 1997143168 | 12/1995 |
| JP | 1997202765 | 8/1997 |
| WO | 8801264 | 2/1988 |

OTHER PUBLICATIONS

Ballou et al., "Tumor labeling in vivo using cyanine-conjugated monoclonal antibodies", Cancer ImmunolImmunother, 1995,41, pp. 257-263.

Licha et al., "New contrast Agents for Optical Imaging: Acid-Cleavable conjugates of Cyanine Dyes with Biomolucules", Part of the SPIE conference on Molucular Imaging: Reporters, Dyes, Markers, and Instrumentation, San Jose, California, Jan. 1999, SPIE vol. 3600, pp. 29-35.

(Continued)

Primary Examiner — Kendra D Carter

(74) Attorney, Agent, or Firm — Dennis A. Bennett; Gale W. Starkey

(57) ABSTRACT

Provided are compounds and compositions of general Formula IX: E1-L-Ar—X-PA, that may be utilized in bioconjugation procedures, where Ar is a chromophore and PA is a functional group capable of being attached to any bioactive molecule of interest. The present invention provides Formulas I-III that are capable of being attached to a bioactive vector for the selective delivery of said photoactive pyrazine derivatives to a desired biological target.

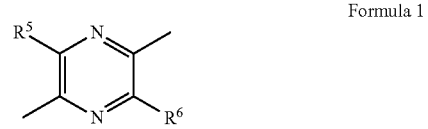

Formula I

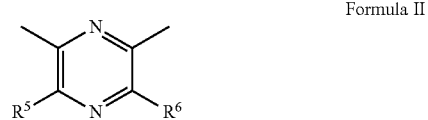

Formula II

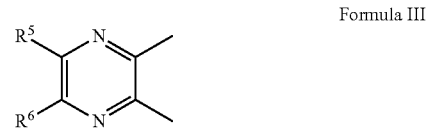

Formula III

14 Claims, 3 Drawing Sheets

(56) References Cited

OTHER PUBLICATIONS

Pandurangi et al., "Chemistry of Bifunctional Photoprobes. e. Correlation between the Efficiencey of CH Insertion by Photolabile Chelating Agents and Lifetimes of Singlet Nitrenes by Flash Photolysis: First Example of Photochemical Attachment of c-Complex with Human Serum Albumin," J. Org. Chem., 1998,63, pp. 9019-9030.
Achilefu et al., "Novel Receptor-Targeted Fluorescent Contrast Agents for In Vivo Tumor Imaging", Investigative Radiology, 2000, vol. 35, No. 8, pp. 479-185.
Moustafa et al., "Synthesis of new pyridoquinoxalines, thienopyridoquinoxalines and pyrimidothienopyridoquinoxalines", Pharmazie, Die, Govi Verlag, Eschborn, DE, 2000, vol. 55, No. 12, pp. 896-899, XP001536673.
Sasalo et al., "Tetrazolo-azido-Isomerisation in Heteroaromatics. I. Syntheses and Reactivities of Some Tetrazolopolyazines", Tetrahedron, 1972, vol. 28, pp. 446-449, XP002450128.
Abushanab et al., "Studies in the Imidaziol[1,5-alpha]pyrazine System", J. Org. Chemistry, 1973, vol. 38, pp. 2049-2052, XP002450129.
Wentrup, "Heteroarylnitrenes-11, Azido/Tetrazoloazine Tautomerisation, and Evidence ofr Nitrene Formation in the Gas:Phase", Tetrahedron, 1970, vol. 26, pp. 4969-4983, XP002450130.
Yu, "Unusual Product in the Photolysate of 2-Azidoxanthone", Chemistry of Heteroycyclic Compounds, 1998, 34(10), p. 1216.
Shirai et al., "Syntheses and Fluorescent Properties of 2,5-Diamino-3,6-dicyanopyrazine Dyes", Dyes and Pigments, 1998, 39(1), 49-68.
Kim et al., "Self-Assembling of Aminopyrazine Fluorescent Dyes and Their Solid State Spectra", Dyes and Pigments, 1998, vol. 39, No. 4, 341-357.
Sekar, Pyrazine dyes: An Update, Colourage, Jan. 1999, 41, 42, 44.
Sato, Studies on Pyrazines. 24[1]. A Simple and Versatile Synthetic Method for 3-Aikozy-and 3-Aminopyrizinecarbonitriles, Heteroycyclic Chem., 1992, 29(7), pp. 1689-1692.
Sato, "Product clas 14: pyrazines", 2004, 16, pp. 751-844.
Zhang et al., "A regioselective synthesis of methyl 7-amino-3-phenylthieno [2m3-b]pyrazine-6-carboxylate", Synthetic Communications, 2001, 32(5), pp. 725-730.
Hnatowich et al., "Radioactive Labeling of Antibody: A Simple and Efficient Method", Science, vol. 220, May 1983, pp. 613-615.
Pelegrin et al., "Photoimmunodiagnosis with antibody-fluorescein conjugates: in vitro and in vivoQreclinical studies", J. Cell Pharmacal, 1992,3, pp. 141-145.
Sandler et al., "Azides", Organic Functional Group Preparations, 1986, pp. 323-349.
Dyall et al., "Pyrolysis of Aryl Azides. Xlt Enhanced Neighbouring Group Effects of Carbonyl in a Locked Conformation", Aust. J. chem.., 1992, 45, pp. 1991-2002.
Cantrell et al., "Repair Synthesis in Human Lymphocytes Provoke by Photolysis of Ethidium Azide", Photochemistry and Photobiology, 1977, vol. 25,Jm. 189-191.

\* cited by examiner

PYRAZINE DERIVATIVES FOR BIOCONJUGATION

CROSS-REFERENCE TO RELATED APPLICATIONS

This application is a continuation-in-part of U.S. patent application Ser. No. 12/281,338, which is a U.S. National Stage Application under 35 U.S.C. §371 of International Application No. PCT/US07/06211, which claims priority to U.S. Provisional patent application Ser. No. 61/781,530, filed Mar. 10, 2006. This application is a continuation-in-part and also claims priority to U.S. application Ser. No. 13/343231, filed Jan. 4, 2012 which is a continuation of U.S. application Ser. No. 11/995,223, filed on 10 Jan. 2008, which is a U.S. National Stage Application under 35 U.S.C. §371 of International Application No. PCT/US07/14370, filed 20 Jun. 2007, and which claims the benefit of priority to U.S. Provisional Application No. 60/815,712 filed on 22 Jun. 2006; and which is a continuation-in-part of U.S. patent application Ser. No. 11/721,186 filed on 8 Jun. 2007, which is a U.S. National Stage Application under 35 U.S.C. §371 of International Application No. PCT/US2005/046732 filed on 22 Dec. 2005, which claims priority to U.S. Provisional Application No. 60/638,611 filed on 23 Dec. 2004. Each of the above-referenced applications is expressly incorporated by reference herein in its entirety.

FIELD OF THE INVENTION

This invention relates generally to photoactive compounds and compositions and their use in photochemical procedures (e.g., medical phototherapeutic procedures).

This invention also relates to pyrazine derivatives that may be characterized as rigid, small molecule dyes capable of absorbing and emanating spectral energy in the visible, near infrared, and/or any other wavelength useful for optical detection. In an embodiment, the present invention relates to pyrazine derivatives that are capable of being attached to a bioactive component for the selective delivery of said photoactive pyrazine derivatives to a desired biological target. The pyrazine derivatives of the present invention are capable of one- and two-photon absorption, and the resultant emission of light can be used for optical detection. In an embodiment, the emission occurs in the red and near infrared (NIR) region of the electromagnetic spectrum.

BACKGROUND

As a preliminary note, various publications are referenced throughout this disclosure by Arabic numerals in brackets. The full citation corresponding to each reference number is listed following the detailed description section. In other instances, the particular reference is cited in the text of the specification. In either situation, the disclosures of these publications are herein incorporated by reference in their entireties in order to fully and clearly describe the state of the art to which this invention pertains.

The use of visible and near-infrared (NIR) light in clinical practice is growing rapidly. Compounds absorbing or emitting in the visible, NIR, or long-wavelength (UV-A, >350 nm) region of the electromagnetic spectrum are potentially useful for optical tomographic imaging, endoscopic visualization, and phototherapy. However, a major advantage of biomedical optics lies in its therapeutic potential. Phototherapy has been demonstrated to be a safe and effective procedure for the treatment of various surface lesions, both external and internal. Its efficacy is comparable to that of radiotherapy, but without the harmful radiotoxicity to critical non-target organs.

Phototherapy has been in existence for many centuries and has been used to treat various skin surface ailments. As early as 1400 B.C. in India, plant extracts (psoralens), in combination with sunlight, were used to treat vitiligo. In 1903, Von Tappeiner and Jesionek used eosin as a photosensitizer for the treatment of skin cancer, lupus of the skin, and condylomata of female genitalia. Over the years, the combination of psoralens and ultraviolet A (low-energy) radiation has been used to treat a wide variety of dermatological diseases including psoriasis, parapsoriasis, cutaneous T-cell lymphoma, eczema, vitiligo, areata, and neonatal bilirubinemia. Although the potential of cancer phototherapy has been recognized since early 1900's, systematic studies to demonstrate safety and efficacy began only in 1967 with the treatment of breast carcinoma. Dougherty et al. subsequently conclusively established that long-term cure is possible with photodynamic therapy (PDT). Currently, phototherapeutic methods are also being investigated for the treatment of some cardiovascular disorders such as atherosclerosis and vascular restenosis, for the treatment rheumatoid arthritis, and for the treatment of some inflammatory diseases such as Crohn's disease.

Phototherapeutic procedures require photosensitizers that have high absorptivity. These compounds should preferably be chemically inert, and become activated only upon irradiation with light of an appropriate wavelength. Light-initiated selective tissue injury can be induced when these photosensitizers bind to target tissues, either directly or through attachment to a bioactive carrier. Furthermore, if the photosensitizer is also a chemotherapeutic agent (e.g. anthracycline antitumor agents), then an enhanced therapeutic effect can be attained.

Effective photochemical agents should have the following properties: (a) large molar extinction coefficient; (b) long triplet lifetime; (c) high yield of singlet oxygen and/or other reactive intermediates, viz., free radicals, nitrenes, carbenes, open-shell ionic species such as cabonium ions and the like; (d) efficient energy or electron transfer to cellular components; (e) low tendency to form aggregation in aqueous milieu; (f) efficient and selective targeting of lesions; (g) rapid clearance from blood and non-target tissues; (h) low systemic toxicity; and (i) lack of mutagenicity. Photosensitizers operate via two distinct pathways, termed Types 1 and 2. The type 1 mechanism is shown in the following scheme:

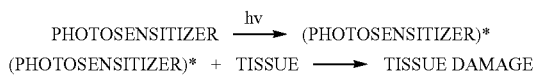

After photoexcitation, the Type 1 mechanism involves direct energy or electron transfer from the photosensitizer to the cellular components, thereby causing cell death. After photoexcitation, the Type 2 mechanism involves distinct steps as shown in the following scheme:

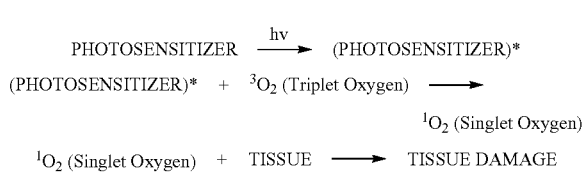

In the first step, singlet oxygen is generated by energy transfer from the triplet excited state of the photosensitizer to the oxygen molecules surrounding the tissues. In the second step, collision of a singlet oxygen with the tissues promotes tissue damage. In both Type 1 and Type 2 mechanisms, the photoreaction proceeds via the lowest triplet state of the photosensitizer. Hence, a relatively long triplet lifetime is required for effective phototherapy. In contrast, for diagnostic imaging purposes, a relatively short triplet lifetime is required to avoid photodamage to the tissue caused by photosensitizers.

The biological basis of tissue injury brought about by tumor phototherapeutic agents has been the subject of intensive study. Various reasonable biochemical mechanisms for tissue damage have been postulated even though the type and number of photosensitizers employed in these studies are relatively small. These biochemical mechanisms are as follows: a) cancer cells upregulate the expression of low density lipoprotein (LDL) receptors, and PDT agents bind to LDL and albumin selectively; (b) porphyrin-like substances are selectively taken up by proliferative neovasculature; (c) tumors often contain an increased number of lipid bodies and are thus able to bind to hydrophobic photosensitizers; (d) a combination of "leaky" tumor vasculature and reduced lymphatic drainage causes porphyrin accumulation; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Most of the currently known photosensitizers are commonly referred to as PDT agents and operate via the Type 2 mechanism. For example, Photofrin II, a hematoporphyrin derivative, was approved by the United States Food and Drug Administration for the treatment of bladder, esophageal, and late-stage lung cancers. However, Photofrin II has been shown to have several drawbacks: low molar absorptivity, ($\epsilon$=3000M$^{-1}$), low singlet oxygen quantum yield (N=0.1), chemical heterogeneity, aggregation, and prolonged cutaneous photosensitivity. Hence, there has been considerable effort in developing safer and more effective photosensitizers for PDT that exhibit improved light absorbance properties, better clearance, and decreased skin photosensitivity compared to those of Photofrin II. These photosensitizers include monomeric porphyrin derivatives, corrins, cyanines, phthalocyanines, phenothiazines, rhodamines, hypocrellins, and the like. However, these phototherapeutic agents also mainly operate via the Type 2 mechanism.

Surprisingly, there has not been much attention directed at developing Type 1 phototherapeutic agents, despite the fact that the Type 1 mechanism seems inherently more efficient than the Type 2 mechanism. First, unlike Type 2, Type 1 photosensitizers do not require oxygen for causing cellular injury. Second, the Type 1 mechanism involves two steps (photoexcitation and direct energy transfer) whereas the Type 2 mechanism involves three steps (photoexcitation, singlet oxygen generation, and energy transfer). Furthermore, some tumors have hypoxic regions that render the Type 2 mechanism ineffective. In spite of the drawbacks associated with the Type 2 mechanism, however, only a small number of compounds have been developed that operate through the Type 1 mechanism, e.g. anthracyline antitumor agents.

Thus, there is a need to develop effective phototherapeutic agents that operate through the Type 1 mechanism. Phototherapeutic efficacy can be further enhanced if the excited state photosensitizers can generate reactive intermediates such as free radicals, nitrenes, carbenes, and the like. These have much longer lifetimes than the excited chromophore and have been shown to cause considerable cell injury.

Targeted delivery of diagnostic and therapeutic agents (generally referred to as 'haptens,' 'effectors,' or 'functional units') such as fluorophores, photosensitizers, radionuclides, paramagnetic agents, and the like to a particular site in the body continues to be of considerable demand in diagnosis, prognosis, and therapy of various lesions [1-4]. The conventional targeting method (referred to as 'bioconjugate approach' or 'pendant design') involves chemical attachment of these agents to bioactive carriers. Bioactive carriers include small molecule drugs, hormones, peptidomimetics, and the like, as well as macromolecular proteins, polysaccharides, polynucleotides, and the like. The bioconjugate approach has been explored extensively over the past several decades, and has met with moderate success, particularly in tumor detection, when medium and large size carriers (c.a. molecular weight >1000 Daltons) are employed [2, 3]. This resulting moderate success is because attachment of the dyes, drugs, metal complexes, or other effector molecules to macromolecular carriers such as antibodies, antibody fragments, or large peptides does not greatly alter the targeting properties; i.e. the bioconjugate is still able to bind to the receptor effectively. This approach, however, is limited because the diffusion of high molecular weight bioconjugates to tumor cells is highly unfavorable, and is further complicated by the net positive pressure in solid tumors [5]. Furthermore, many dyes in general, tend to form aggregates in aqueous media that lead to fluorescence quenching. Therefore, there is a need to prepare photoactive small molecules that are not only intrinsically useful for biomedical non-medical optical applications, but also are capable of attachment to suitable bioactive molecules.

Accordingly, a need remains for new small molecule dyes capable of absorbing and emanating spectral energy in the visible and/or near infrared spectrum. Pyrazines are a class of photostable small molecules having highly desirable photophysical properties useful for biomedical applications.

A

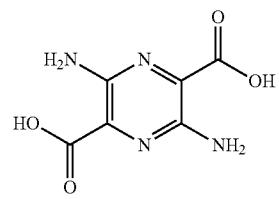

$\lambda_{abs}$: 410 nm
$\lambda_{em}$: 480 nm

B

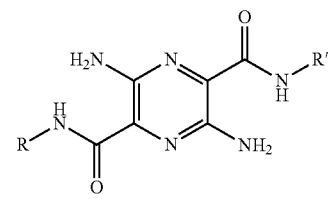

$\lambda_{abs}$: 430-450 nm
$\lambda_{em}$: 550-560 nm

-continued

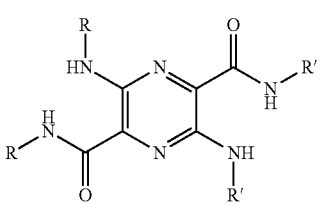

$\lambda_{abs}$: 480-500 nm
$\lambda_{em}$: 585-605 nm

Pyrazine derivatives containing electron withdrawing groups at the 2,5 positions and electron donating groups at the 3,6 positions such as 3,6-diamino-2,5-pyrazine-dicarboxylic acid (structure A) and the corresponding amides strongly absorb and emit in the blue to orange regions with a large Stokes shift on the order of ~100 nm and with fluorescence quantum yields of about 0.4 [6,7] Conversion of the carboxyl group in 1 to the secondary amide derivatives (structure B) produces a bathochromic shift of about 40 nm, and alkylation of the amino group (structure C) results in further red shift of about 40 nm. Hence, the pyrazine scaffold presents an attractive opportunity to 'tune' the electronic properties.

SUMMARY

Photochemical Procedures

In one regard, the present invention discloses novel organic compounds and compositions that may be utilized in photochemical procedures. A photochemical procedure encompasses both medical therapeutic and diagnostic procedures, as will be subsequently described.

A first aspect of the invention is directed to a compound having the general formula E1-L-Ar-X-PA, where Ar is a photosensitizer, PA is a photoactive compound, and each of E1, L, and X is optional.

The photosensitizer (Ar) is a chromophore that generally contains large cyclic or aromatic rings. The photosensitizer may be linked either directly or indirectly to E1, which in some embodiments can be selected to target the compound to a specific site, or which in other embodiments can be hydrogen. The photosensitizer (Ar) is linked directly or indirectly to a photoactive compound (PA) that, when photoactivated, additionally damages tissues via a Type 1 or Type 2 mechanism. It will be appreciated that, by selecting specific components for E1, one can target the compound to reach a specific body site, for example, a tumor site where photoactivation will destroy tumor cells. It will also be appreciated that a linker L, if present, can be selected to appropriately link E1 to the photosensitizer (Ar). For instance, in some embodiments, it may be desirable to select a linker (L) that will provide a desired amount of space between E1 and a bulky aromatic or cyclic photosensitizer.

PA is a photoactive compound such as an azide, diazoalkane, peroxide, alkyliodide, sulfenate, azidoalkyl, azidoaryl, diazoalkyl, diazoaryl, peroxoalkyl, peroxoaryl, iodoalkyl, azoalkyl, cyclic or acyclic azoalkyl, sulfenatoalkyl, sulfenatoaryl, etc. that produce nitrenes, free radicals, carbenes, etc. upon photoactivation.

Numerous combinations of Ar and PA are possible to provide Type 1 phototherapy, as will be described. Additionally, it will be appreciated that many formulations are possible because of the various linkers and targeting moieties that may be used, as will also be described.

Ar is a photosensitizer including at least one substituent represented by any of formulas I-VIII

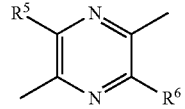

Formula I

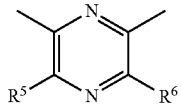

Formula II

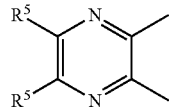

Formula III

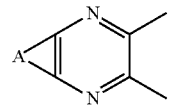

Formula IV

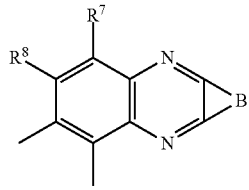

Formula V

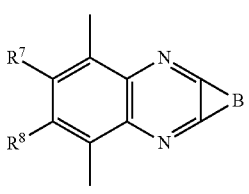

Formula VI

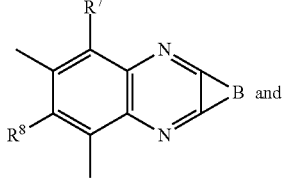

Formula VII and

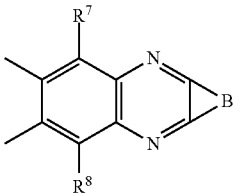

Formula VIII

E1, if present, may be hydrogen or a targeting moiety. For instance, in some embodiments, E1 may be a receptor binding molecule, such as a whole or fragmented somatostatin receptor binding molecule, whole or fragmented ST receptor binding molecule, whole or fragmented neurotensin receptor binding molecule, whole or fragmented bombesin receptor binding molecule, whole or fragmented cholecystekinin (CCK) receptor binding molecule, whole or fragmented steroid receptor binding molecule, or whole or fragmented carbohydrate receptor binding molecule.

X, if present, is a linker between the photosensitizer (Ar) and the photoactive compound (PA) and may be selected from a single bond, —(CH$_2$)$_a$—, —CO—, —OCO—, —HNCO—, —(CH$_2$)$_a$CO—, —(CH$_2$)$_a$OCO—, C$_1$-C$_{10}$ alkyl, C$_5$-C$_{10}$ aryl, C$_5$-C$_{10}$ heteroaryl, C$_1$-C$_{10}$ acyl, nitro, cyano, —(CH$_2$)$_a$CO$_2$—, —(CH$_2$)$_a$NR$^1$—, —NR$^1$CO—, —(CH$_2$)$_a$CONR$^1$—, —(CH$_2$)$_a$SO—, —(CH$_2$)$_a$SO$_2$—, —(CH$_2$)$_a$CON(R$^1$)—, —(CH$_2$)$_a$N(R$^1$)CO—, —(CH$_2$)$_a$N(R$^1$)CON(R$^2$)— and —(CH$_2$)$_a$N(R$^1$)CSN(R$^2$)—.

L, if present, is a linker between the photosensitizer (Ar) and E1 and may be selected from a single bond, —HNCO—, —CONR$^3$—, —(CH$_2$)$_b$—, —(CH$_2$)$_b$CONR$^3$—, —N(R$^3$)CO(CH$_2$)$_b$—, —OCO(CH$_2$)$_b$—, —(CH$_2$)$_b$CO$_2$—, —OCONH—, —OCO$_2$—, —HNCONH—, —HNCSNH—, —HNNHCO—, —OSO$_2$—, —NR$^3$(CH$_2$)$_b$CONR$^4$—, —CONR$^3$(CH$_2$)$_b$NR$^4$CO—, —NR$^3$CO(CH$_2$)$_b$CONR$^4$—, —(CH$_2$)$_b$CON(R$^3$)—, —(CH$_2$)$_b$N(R$^3$)CO—, —(CH$_2$)$_b$N(R$^3$)CON(R$^4$)— and —(CH$_2$)$_b$N(R$^3$)CSN(R$^4$)—.

In the above structures, each of R$^1$ to R$^4$ may independently be selected from hydrogen, C1-C10 alkyl, —OH, C5-C10 aryl, C1-C10 hydroxyalky, C1-C10 polyhydroxyalkyl, C1-C10 alkoxyl, C1-C10 alkoxyalkyl, —SO$_3$H, —(CH$_2$)$_c$CO$_2$H and —(CH$_2$)$_c$NR$^9$R$^{10}$.

Each of R$^9$ and R$^{10}$ may independently be selected from hydrogen, C1-C10 alkyl, C5-C10 aryl and C1-C10 polyhydroxyalkyl.

Each of a, b, and c may independently range from 0 to 10.

Each of A and B may independently be selected from —(CH$_2$)$_d$Y(CH$_2$)$_e$—, —C(R$^{11}$)=C(R$^{12}$)—C(R$^{13}$)=C(R$^{14}$)—, —N=C(R$^{13}$)=C(R$^{13}$)=C(R$^{14}$)—, —C(R$^{11}$)=N—C(R$^{13}$)=C(R$^{14}$)—, —C(R$^{11}$)=C(R$^{12}$)—N=C(R$^{14}$)—, —C(R$^{11}$)=C(R$^{12}$)—C(R$^{13}$)=N—, —C(R$^{11}$)=C(R$^{12}$)—N(R$^{15}$)—, —C(R$^{11}$)=C(R$^{12}$)—O—, —C(R$^{11}$)=C(R$^{12}$)—S—, —N=C(R$^{11}$)—N(R$^{15}$)—, —N=C(R$^{11}$)—O—, —N=C(R$^{11}$)S—, —C(R$^{11}$)=N—N(R$^{15}$)—, —C(R$^{11}$)=N—N(R$^{15}$)—, —C(R$^{11}$)=N—O—, —N=N—N(R$^{15}$)— and —N=N—O— or —N=N—S—;

Y may be selected from —O—, —NR$^{16}$—, —S—, —SO— or —SO$_2$—.

Each of d and e may independently vary from 0 to 3.

R$^{16}$ may be selected from hydrogen, C$_1$-C$_{10}$ alkyl, C$_5$-C$_{10}$ aryl, C$_1$-C$_{10}$ hydroxyalkyl, and C$_1$-C$_{10}$ alkoxyalkyl.

Each of R$^5$ to R$^8$ and each of R$^{11}$ to R$^{15}$ may independently be selected from hydrogen, C$_1$-C$_{10}$ alkyl, C$_5$-C$_{10}$ aryl, C$_1$-C$_{10}$ hydroxyalkyl, C$_1$-C$_{10}$ alkoxyalkyl, C$_5$-C$_{10}$ heteroaryl, C$_1$-C$_{10}$ acyl, nitro, cyano, —(CH$_2$)$_f$N$_3$, —(CH$_2$)$_f$CO$_2$R$^{16}$, —(CH$_2$)$_f$NR$^{16}$R$^{17}$, —NR$^{16}$CON$_3$, —(CH$_2$)$_f$CONR$^{16}$R$^{17}$, —(CH$_2$)$_f$CON$_3$, —(CH$_2$)$_f$SON$_3$, —(CH$_2$)$_f$SO$_2$N$_3$, —(CH$_2$)$_f$CON(R$^{16}$)E2, —(CH$_2$)$_f$N(R$^{16}$)COE2, —(CH$_2$)$_f$N(R$^{16}$)CON(R$^{17}$)E2 and —(CH$_2$)$_f$N(R$^{16}$)CSN(R$^{17}$)E2.

f may vary from 0 to 10.

Each of R$^{16}$ and R$^{17}$ may be independently selected from hydrogen, C$_1$-C$_{10}$ alkyl, C$_5$-C$_{10}$ aryl, C$_1$-C$_{10}$ hydroxyalkyl and C$_1$-C$_{10}$ alkoxyalkyl.

Each of E1 and E2 may independently be hydrogen or a targeting moiety.

In some embodiments, E1 and E2, if present, are each independently a whole or fragmented somatostatin receptor binding molecule, whole or fragmented ST receptor binding molecule, whole or fragmented neurotensin receptor binding molecule, whole or fragmented bombesin receptor binding molecule, whole or fragmented CCK receptor binding molecule, whole or fragmented steroid receptor binding molecule, and whole or fragmented carbohydrate receptor binding molecule. In some embodiments, E1 and E2 are both receptor binding molecules of the same type. For instance, in some embodiments, E1 and E2 are both a whole or fragmented somatostatin receptor binding molecule, whole or fragmented ST receptor binding molecule, whole or fragmented neurotensin receptor binding molecule, whole or fragmented bombesin receptor binding molecule, whole or fragmented CCK receptor binding molecule, whole or fragmented steroid receptor binding molecule, and whole or fragmented carbohydrate receptor binding molecule. In some embodiments, E1 may be a receptor binding molecule of a first type, and E2 may be a receptor binding molecule of a second type different from E1.

For targeting purposes, external attachment of a targeting moiety may be used. If photoactive compounds and/or photosensitizers themselves preferentially accumulate in a target tissue, however, such a targeting moiety may not be needed. For example, if Ar is an anthracycline moiety, it may tend to bind to cancer cells directly and not require a targeting moiety. Thus, E1 may be absent or may be hydrogen. A targeting moiety includes but is not limited to one or more specific sites of a molecule which will bind to a particular complementary site, such as the specific sequence of amino acids in a region of an antibody that binds to the specific antigen binding site. A targeting moiety is not limited to a particular sequence or site, but includes anything that will target an inventive compound and/or composition to a particular anatomical and/or physiological site. Examples of compounds that may be used as targeting moieties include, but are not limited to, whole receptor binding compounds or fragments of receptor binding compounds.

A second aspect of the present invention is directed to a biocompatible composition including at least one biocompatible excipient (e.g., a buffer, emulsifier, surfactant, electrolyte, or combination thereof) and a compound having the general formula E1-L-Ar-X-PA as described herein.

In some embodiments of this second aspect, a liposome may be utilized as a carrier or vehicle for the composition. For example, in some embodiments, the photosensitizer may be a part of the lipophilic bilayers, and the targeting moiety, if present, may be on the external surface of the liposome. As another example, a targeting moiety may be externally attached to the liposome after formulation for targeting the liposome (which contains the inventive compound) to the desired tissue, organ, or other site in the body.

Still a third aspect of the invention is directed to a method of using a compound of the general formula E1-L-Ar-X-PA described herein. In this method, an effective amount of the compound (e.g., as a component of a biocompatible composition) is administered to a target tissue in an animal. The target tissue is then exposed to light sufficient to activate the compound. The compound may be allowed to accumulate in the target tissue before the target tissue is exposed to light (e.g., light having a wavelength between about 300 and 950 nm). In some embodiments, the compound may be used in a phototherapeutic procedure in which the target tissue is exposed to light of sufficient power and fluence rate to photoactivate the compound and perform phototherapy. Incidentally, photoexcitation of the aromatic photosensitizers of formulas I-VIII effects a rapid intramolecular energy transfer to PA, resulting in bond rupture and production of nitrene and nitrogen gas. The nitrogen that is released is in a vibrational excited state, which may cause additional cellular injury.

Bioconjugation Procedures and Uses

In another regard, the present invention discloses compounds and compositions of general formula: E1-L-Ar-X-PA (Formula IX) where Ar is a pyrazine group; PA is a functional group capable of being attached to any bioactive molecule of interest; E1 may be present or absent and E1 if present, is hydrogen or a targeting moiety; and L and X are linking moieties. Pyrazine groups are useful for bioconjugate applications because pyrazine groups have absorption and emission/fluorescence in the visible region, and exhibit large Stokes shifts. These properties allow flexibility in both tuning a molecule to a desired wavelength and introducing a variety of biomolecules to provide targeting properties. In embodiments, compounds and compositions of Formula IX can be used in bioconjugation procedures and for other uses, including therapeutic and diagnostic procedures.

In embodiments of this aspect of the invention described by Formula IX, PA is an attachment group containing hydrogen, $C_1$-$C_{10}$ alkyl, vinyl, ethynyl, $C_5$-$C_{10}$ aryl, hydroxyl, carboxyl, amino, mercapto, succinimidyloxycarbonyl, cyano, isocyanato, isothiocyanato, maleimido, and azido. In an embodiment of this aspect of the invention described by Formula IX, PA does not contain an azide or azido group. In an embodiment of this aspect of the invention described by Formula IX, PA includes a maleimide group. A maleimide group present on the compound is useful for reacting to a free sulfhydryl group. In an embodiment of this aspect of the invention described by Formula IX, PA includes a NHS ester group. In embodiments of this aspect of the invention described by Formula IX, PA is comprises a group that allows attachment to a bioactive molecule.

In embodiments of this aspect of the invention described by Formula IX above, Ar is a pyrazine group of Formulas I-III:

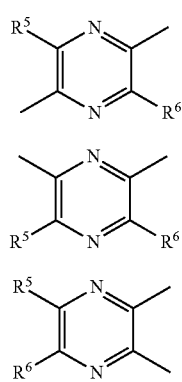

Formula I

Formula II

Formula III where the lines indicate the attachment to the L and X groups, if present.

For targeting purposes, compounds of Formula IX are attached to a targeting moiety using reactions known in the art and described herein. A targeting moiety is not limited to a particular sequence or site, but includes anything that will target an inventive compound and/or composition to a particular anatomical and/or physiological site. Examples of compounds that may be used as targeting moieties include, but are not limited to compounds of Formula IX chemically or physically bound to whole receptor binding compounds or fragments of receptor binding compounds through variable PA or E1. In some embodiments, the targeting moiety is a receptor binding molecule, such as a whole or fragmented somatostatin receptor binding molecule, whole or fragmented ST receptor binding molecule, whole or fragmented neurotensin receptor binding molecule, whole or fragmented bombesin receptor binding molecule, whole or fragmented CCK receptor binding molecule, whole or fragmented steroid receptor binding molecule, or a whole or fragmented carbohydrate receptor binding molecule.

The present invention is also directed to a biocompatible composition including at least one biocompatible excipient (e.g., a buffer, emulsifier, surfactant, electrolyte, or combination thereof) and a compound having the general Formula IX as described herein.

In some embodiments of this aspect of the invention, a liposome may be utilized as a carrier or vehicle for the composition of Formula IX. For example, in some embodiments, the compound of Formula IX may be a part of the lipophilic bilayers, and the targeting moiety, if present, may be on the external surface of the liposome. As another example, a targeting moiety may be externally attached to the liposome after formulation for targeting the liposome (which contains the inventive compound) to the desired tissue, organ, or other site in the body.

Still another aspect of the invention is directed to a method of using a compound of the general Formula IX described herein. In this method, an effective amount of the compound (e.g., as a component of a biocompatible composition) is administered to a target tissue in an animal. The target tissue is then exposed to light sufficient to activate the compound. The compound may be allowed to accumulate in the target tissue before the target tissue is exposed to visible and/or infrared light (e.g., light having a wavelength between about 300 and 950 nm). In an embodiment, the emitted light is detected.

These and other embodiments of the inventive compounds, compositions, and methods will be apparent in light of the following figures, description, and examples.

DETAILED DESCRIPTION

Photochemical Procedures

Figure 1A:
FIG. 1A is a general Type 1 photoactivation scheme.
Figure 1A:
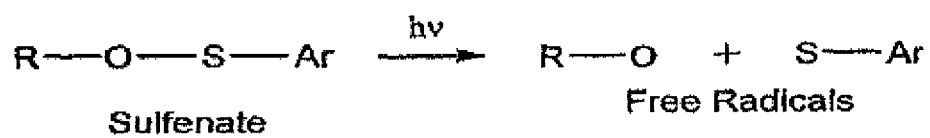
Figure 1A:
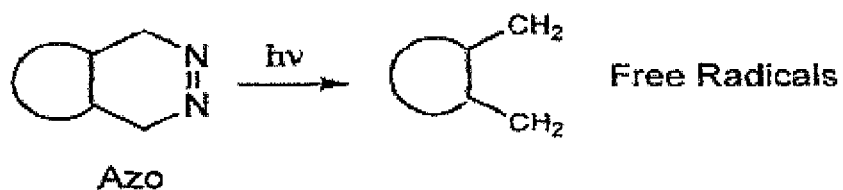
Figure 1B:
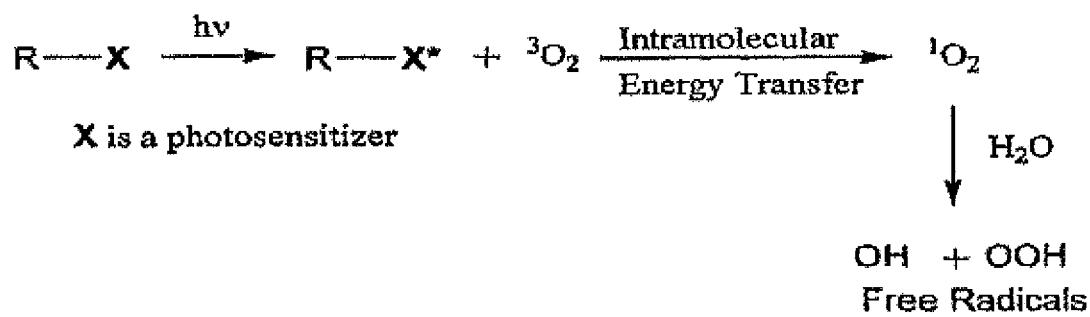
FIG. 1B is a general Type 2 photoactivation scheme.

The invention discloses novel organic compounds, compositions, and photochemical procedures. A photochemical procedure encompasses any type of biologic procedure using the inventive compounds, and includes in vivo and in vitro procedures, and therapeutic and diagnostic procedures. The following is a detailed description of various embodiments of exemplary compounds of the general formula E1-L-Ar-X-PA.

PA is a photoactive compound that includes an azide, diazoalkane, peroxide, alkyliodide, sulfenate, azidoalkyl, azidoaryl, diazoalkyl, diazoaryl, peroxoalkyl, peroxoaryl, iodoalkyl, azoalkyl, cyclic and/or acyclic azoalkyl, sulfenatoalkyl, or sulfenatoaryl.

Ar is a photosensitizer that is an aromatic or a heteroaromatic chromophore containing at least one of formulas I-VIII

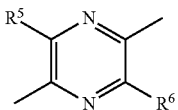

Formula I

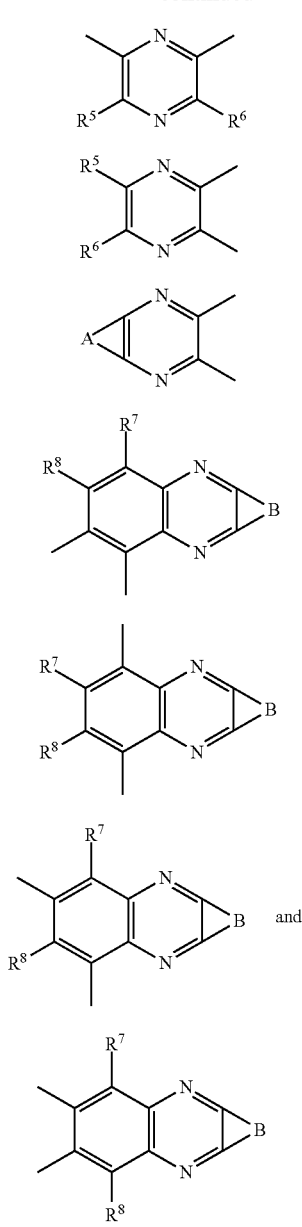

Formula II

Formula III

Formula IV

Formula V

Formula VI

Formula VII

Formula VIII

E1, if present, is either hydrogen or a targeting moiety. Again, a targeting moiety generally refers to a particular region of the compound that is recognized by, and binds to, a target cell, tissue, organ, etc. A targeting moiety may include an antibody (all or a portion, and monoclonal or polyclonal), peptide, peptidomimetic, carbohydrate, glycomimetic, drug, hormone, nucleic acid, lipid, albumin, receptor binding molecule, inclusion compound (a compound that has a cavity with a defined volume such that it can incorporate small molecules or a part of a small molecule) such as cyclodextrins (cyclodextrins can accommodate hydrophobic residues such as adamantine, benzene, etc), etc.

Targeting moieties may be part of a biomolecule which include hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. Specific examples of targeting moieties include steroid hormones for the treatment of breast and prostate lesions, whole or fragmented somatostatin, bombesin, and neurotensin receptor binding molecules for the treatment of neuroendocrine tumors, whole or fragmented cholecystekinin receptor binding molecules for the treatment of lung cancer, whole or fragmented heat sensitive bacterioendotoxin (ST) receptor and carcinoembryonic antigen (CEA) binding molecules for the treatment of colorectal cancer, dihydroxyindolecarboxylic acid and other melanin producing biosynthetic intermediates for melanoma, whole or fragmented integrin receptor and atherosclerotic plaque binding molecules for the treatment of vascular diseases, and whole or fragmented amyloid plaque binding molecules for the treatment of brain lesions. In some embodiments, E1, if present, is selected from octreotide and octreotate peptides, heat-sensitive bacterioendotoxin receptor binding peptide, carcinoembryonic antigen antibody (anti-CEA), bombesin receptor binding peptide, neurotensin receptor binding peptide, cholecystekinin receptor binding peptide, or estrogen.

As a non-limiting example, and with respect to compounds that may be used as E1 because they bind to a receptor, one skilled in the art would appreciate that diethylstilbesterol is not a steroid but strongly binds to the estrogen receptor (a steroid receptor); testosterone does not bind to the estrogen receptor, testosterone and esterone do not bind to the corticosteroid receptors, cortisone and aldosterone do not bind to the sex hormone receptors, and the following compounds are known to bind to the estrogen receptor, namely, estratriol, 17β-aminoestrogen (AE) derivatives such as prolame and butolame, drugs such as tamoxifen, ICI-164384, raloxifene, genistein, 17β-estradiol, glucocorticoids, progesterone, estrogens, retinoids, fatty acid derivatives, phytoestrogens, etc. Thus, one skilled in the art would know how to select compounds to target and/or to avoid a particular site.

For targeting purposes, an external attachment of a targeting moiety is usually desirable unless the compounds themselves preferentially accumulate in the target tissue, thereby obviating the need for an additional binding group. For example, administering delta-aminolevulinic acid, an intermediate in porphyrin biosynthesis, results in a two-fold uptake of porphyrins in tumors compared to normal tissues. Similarly, administering dihydroxyindole-2-carboxylic acid, an intermediate in melanin biosynthesis, produces substantially enhanced levels of melanin in melanoma cells compared to normal cells. Thus, an inventive compound may be delivered to the site of a lesion by attaching it to these types of biosynthetic intermediates. Although this targeting is less specific than in embodiments where a specific targeting moiety is included in the compound, it still targets the compound to a desired site and thus is another embodiment of the invention.

X, if present, is a linker between the photosensitizer (Ar) and the photoactive compound (PA) and is selected from a single bond, $-(CH_2)_a-$, $-CO-$, $-OCO-$, $-HNCO-$, $-(CH_{2a}CO-$, $-(CH_2)_aOCO-$, $C_1-C_{10}$ alkyl, $C_5-C_{10}$ aryl, $C_5-C_{10}$ heteroaryl, $C_1-C_{10}$ acyl, nitro, cyano, $-(CH_2)_aCO_2-$, $-(CH_2)_aNR^1-$, $-NR^1CO-$, $-(CH_2)_aCONR^1-$, $-(CH_2)_aSO-$, $-(CH_2)_aSO_2-$, $-(CH_2)_aCON(R^1)-$, $-(CH_2)_aN(R^1)CO-$, $-(CH_2)_aN(R^1)CON(R^2)-$ and $-(CH_2)_aN(R^1)CSN(R^2)-$.

L, if present, is a linker between the photosensitizer and E1 and is selected from a single bond, $-HNCO-$, $-CONR^3$, $-(CH_2)_b-$, $-(CH_2)_bCONR^3-$, $-N(R^3)CO(CH_2)_b-$, $-OCO(CH_2)_b-$, $-(CH_2)_bCO_2-$, $-OCONH-$, $-OCO_2-$, $-HNCONH-$, $-HNCSNH-$, $-HNNHCO-$, $-OSO_2-$, $-NR^3(CH_2)_bCONR^4-$, —CONR$^3$(CH$_2$)$_b$NR$^4$CO—, —NR$^3$CO(CH$_2$)$_b$CONR$^4$—, —(CH$_2$)$_b$CON(R$^3$)—, —(CH$_2$)$_b$N(R$^3$)CO—, —(CH$_2$)$_b$N(R$^3$)CON(R$^4$)— and —(CH$_2$)$_b$N(R$^3$)CSN(R$^4$)—.

Each of R$^1$ to R$^4$ is independently selected from hydrogen, C1-C10 alkyl, —OH, C5-C10 aryl, C1-C10 hydroxyalky, C1-C10 polyhydroxyalkyl, C1-C10 alkoxyl, C1-C10 alkoxyalkyl, —SO$_3$H, —(CH$_2$)$_c$CO$_2$H, and —(CH$_2$)$_c$NR$^9$R$^{10}$.

Each R$^9$ and R$^{10}$ is independently selected from hydrogen, C1-C10 alkyl, C5-C10 aryl, and C1-C10 polyhydroxyalkyl.

Each of a, b, and c independently ranges from 0 to 10.

Each of A and B is independently selected from —(CH$_2$)$_d$Y(CH$_2$)$_e$—, —C(R$^{11}$)=C(R$^{12}$)—C(R$^{13}$)=C(R$^{14}$)—, —N=C(R$^{12}$)—C(R$^{13}$)=C(R$^{14}$)—, —C(R$^{11}$)=N—C(R$^{13}$)=C(R$^{14}$), —C(R$^{11}$)=C(R$^{12}$)—N=C(R$^{14}$)—, —C(R$^{11}$)=C(R$^{12}$)—C(R$^{13}$)=N—, —C(R$^{11}$)=C(R$^{12}$)—N(R$^{15}$)—, —C(R$^{11}$)=C(R$^{12}$)—O—, —C(R$^{11}$)=C(R$^{12}$)—S—, —N=C(R$^{11}$)—N(R$^{15}$)—, —N=C(R$^{11}$)—O—, —N=C(R$^{11}$)—S—, —C(R$^{11}$)=N—N(R$^{15}$)—, —C(R$^{11}$)=N—N(R$^{15}$)—, —C(R$^{11}$)=N—O—, —N=N—N(R$^{15}$)— and —N=N—O— or —N=N—S—.

Y is selected from —O—, —NR$^{16}$—, —S—, —SO— and —SO$_2$—.

Each of d and e independently vary from 0 to 3.

R$^{16}$ is selected from hydrogen, C$_1$-C$_{10}$ alkyl, C$_5$-C$_{10}$ aryl, C$_1$-C$_{10}$ hydroxyalkyl, or C$_1$-C$_{10}$ alkoxyalkyl.

Each of R$^5$ to R$^8$ and each of R$^{11}$ to R$^{15}$ is independently selected from hydrogen, C$_1$-C$_{10}$ alkyl, C$_5$-C$_{10}$ aryl, C$_1$-C$_{10}$ hydroxyalkyl, C$_1$-C$_{10}$ alkoxyalkyl, C$_5$-C$_{10}$ heteroaryl, C$_1$-C$_{10}$ acyl, nitro, cyano, —(CH$_2$)$_f$N$_3$, —(CH$_2$)$_f$CO$_2$R$^{16}$, —(CH$_2$)$_f$NR$^{16}$R$^{17}$, —NR$^{16}$CON$_3$, —(CH$_2$)$_f$CONR$^{16}$R$^{17}$, —(CH$_2$)$_f$CON$_3$, —(CH$_2$)$_f$SON$_3$, —(CH$_2$)$_f$SO$_2$N$_3$, —(CH$_2$)$_f$CON(R$^{16}$)E2, —(CH$_2$)$_f$N(R$^{16}$)COE2, —(CH$_2$)$_f$N(R$^{16}$)CON(R$^{17}$)E2 and —(CH$_2$)$_f$N(R$^{16}$)CSN(R$^{17}$)E2.

f varies from 0 to 10.

Each of R$^{16}$ and R$^{17}$ is independently selected from hydrogen, C$_1$-C$_{10}$ alkyl, C$_5$-C$_{10}$ aryl, C$_1$-C$_{10}$ hydroxyalkyl and C$_1$-C$_{10}$ alkoxyalkyl.

E2 is defined in the same manner as E1, and each occurrence of E1 and E2 is independently hydrogen or a targeting moiety.

Compounds of the invention may be used in compositions and in vitro or in vivo biological procedures. Conjugation of a small molecule to a small peptide or other small molecule carrier generally preserves receptor binding capability. Coupling of diagnostic and radiotherapeutic agents to biomolecules can be accomplished by methods well known in the art, as disclosed in Hnatowich et al., Radiolabeling of Antibodies: A simple and efficient method. *Science*, 1983, 220, 613; A. Pelegrin et al., Photoimmunodiagnostics with antibody-fluorescein conjugates: in vitro and in vivo preclinical studies. *Journal of Cellular Pharmacology*, 1992, 3, 141-145, and U.S. Pat. No. 5,714,342, which are expressly incorporated by reference herein in their entirety.

Formulas I-VIII are members of a class of small molecules that possess desirable absorption and emission properties in the UV-A, visible and NIR region of the electromagnetic spectrum. Various substituents such as electron donating groups, electron withdrawing groups, lipophilic groups, or hydrophilic groups can be attached at the respective carbon atoms for altering physicochemical and/or biological properties, as known to one skilled in the art. The substituents may also optionally include E2 (which is either hydrogen or a targeting moiety) that will selectively bind to a desired target tissue or lesion. The target may be a biological receptor, an enzyme, etc.

In some embodiments, at least the photosentizer (Ar) of the compound operates through a Type 1 photoactive mechanism capable of generating reactive intermediates such as free radicals, nitrenes, carbenes, and the like that can result in injury or death to cells when the photochemically active compound is at a target site such as a tumor or lesion. Compounds of the invention absorb radiation in the low-energy, ultraviolet, visible, or NIR region of the electromagnetic spectrum, and are useful for photodiagnosis, phototherapy, etc. of tumors and other lesions. In some embodiments, the photosensitizer (Ar) portion of the compound may be tuned (e.g., via substitution of the π system) to customize electronic and/or optical properties of the photosensitizer. For instance, it may be desirable to tune a photosensitizer so that it absorbs in the visible red region of the spectrum and operates through a Type 2 photoactive mechanism.

As previously described, Type 1 agents contain a labile precursor that undergoes photofragmentation upon direct irradiation with light of a desired wavelength, and produce reactive intermediates such as nitrenes, carbenes, or free radicals from photoactive compounds (PA). PA may be azides, diazoalkanes, peroxides, alkyliodides, sulfenates, azidoalkyl, azidoaryl, diazoalkyl, diazoaryl, peroxoalkyl, peroxoaryl, iodoalkyl, azoalkyl, cyclic or acyclic azoalkyl, sulfenatoalkyl, sulfenatoaryl, etc. For example, azides (R—N$_3$) produce nitrenes (R—N:); diazoalkanes (R—CHN$_2$) produce carbenes (R—CH:); peroxides (RO—OR) produce alkoxy radicals (RO.); alkyl iodides (R—I) produce alkyl radicals (R.); and sulfenates (RS—OR) produce alkoxy radicals (RO.) and mercapto radicals (RS.). Alternatively, the reactive intermediates can be produced indirectly by exciting an aromatic photosensitizer; for example, Ar can transfer energy intramolecularly to an azide or other photoactive group and cause fragmentation.

Figure 2A:
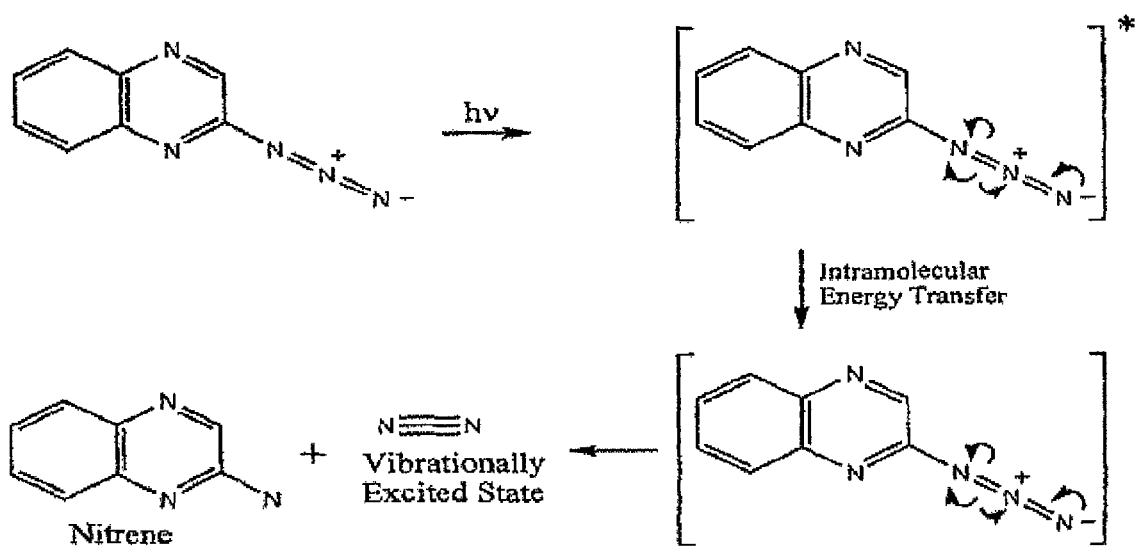
FIG. 2A is a photoactivation scheme showing formation of diradicals.
Figure 2B:
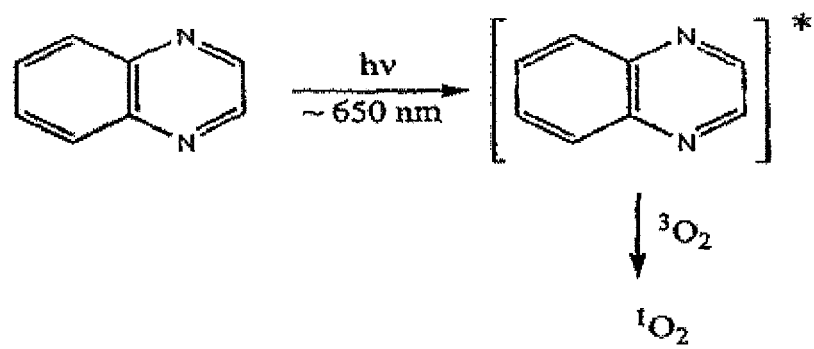
FIG. 2B is a photoactivation scheme showing formation of singlet oxygen.

Photoactivation of photosensitizers of formulas I-VIII to produce nitrenes, renders such photosensitizers useful for Type 1 phototherapy, shown schematically in FIGS. 1 and 2A. Photoexcitation of Ar effects rapid intramolecular energy transfer to the azido group, resulting in bond rupture and production of nitrene and nitrogen gas. Photoexcitation of the aromatic photosensitizers effects rapid intramolecular energy transfer to the azide group, resulting in N—N bond rupture with concomitant extrusion of molecular nitrogen and formation of nitrene. The nitrogen that is released upon photofragmentation is in a vibrational excited state that, upon relaxation, releases the energy to its surroundings in the form of heat that will result in tissue damage as well. Aliphatic azido compounds can also be used for phototherapy, but may require high-energy light for activation unless the azide moiety is attached to conjugated polyene system.

Photosensitizers of Formulas I-VIII may absorb in the red region of the electromagnetic spectrum and can transfer energy to oxygen molecules to generate singlet oxygen species. In some embodiments, photosensitizers of formulas I-VIII and bioconjugates thereof may be tuned to absorb in the red region and are, therefore, useful for Type 2 phototherapy.

The photosensitizers of Formulas I-VIII tend to have functional groups that absorb light in the visible region of the spectrum. They induce intramolecular energy transfer that results in photofragmentation of photoactive compounds such as azides, sulfenates, azo compounds, azidoalkyl, azidoaryl, diazoalkyl, diazoaryl, peroxoalkyl, peroxoaryl, iodoalkyl, azoalkyl, cyclic or acyclic azoalkyl, sulfenatoalkyl, sulfenatoaryl, etc. The photosensitizers of Formulas I-VIII are useful due to their small size and photophysical properties, in additional to their photochemical properties.

An exemplary embodiment of a compound of the invention that exhibits the general formula E1-L-Ar-X-PA is described below.

Ar is a photosensitizer selected from the Formulas I-VIII below;

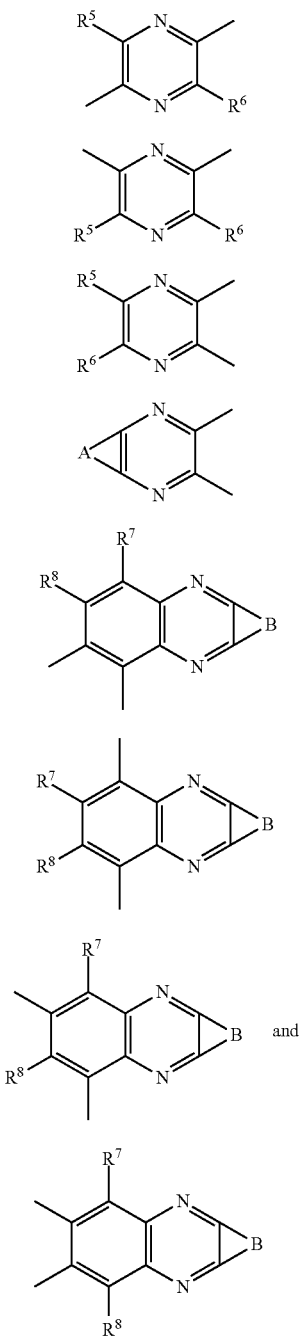

Formula I

Formula II

Formula III

Formula IV

Formula V

Formula VI

Formula VII and

Formula VIII

PA is selected from azide, azidoalkyl, azidoaryl, diazoalkyl, diazoaryl, peroxoalkyl, peroxoaryl, iodoalkyl, azoalkyl, cyclic or acyclic azoalkyl, sulfenatoalkyl, and sulfenatoaryl;

X, if present, is either a single bond or is selected from —$(CH_2)_a$—, —CO—OCO—, —HNCO—, —$(CH_2)_a$CO—, —$(CH_2)_a$OCO—, $C_1$-$C_{10}$ alkyl, $C_5$-$C_{10}$ aryl, $C_5$-$C_{10}$ heteroaryl, $C_1$-$C_{10}$ acyl, nitro, cyano, —$(CH_2)_a$$CO_2$—, —$(CH_2)_a$$NR^1$—, —$NR^1CO$—, —$(CH_2)_a$$CONR^1$—, —$(CH_2)_a$SO—, —$(CH_2)_a$$SO_2$—, —$(CH_2)_a$$CON(R^1)$—, —$(CH_2)_a$$N(R^1)CO$—, —$(CH_2)_a$$N(R^1)CON(R^2)$— and —$(CH_2)_a$$N(R^1)CSN(R^2)$—;

L, if present, is a linker between the photosensitizer and the targeting moiety and is selected from —HNCO—, —$CONR^3$—, —$(CH_2)_b$—, —$(CH_2)_b$$CONR^3$—, —$N(R^3)CO$$(CH_2)_b$—, —$OCO(CH_2)_b$—, —$(CH_2)_b$$CO_2$—, —OCONH—, —$OCO_2$—, —HNCONH—, —HNCSNH—, —HNNHCO—, —$OSO_2$—, —$NR^3(CH_2)_b$$CONR^4$—, —$CONR^3(CH_2)_b$$NR^4CO$—, —$NR^3CO(CH_2)_b$$CONR^4$—, —$(CH_2)_b$$CON(R^3)$—, —$(CH_2)_b$$N(R^3)CO$—, —$(CH_2)_b$$N(R^3)CON(R^4)$—, and —$(CH_2)_b$$N(R^3)CSN(R^4)$—;

each of $R^1$ to $R^4$ is independently selected from hydrogen, C1-C10 alkyl, —OH, C5-C10 aryl, C1-C10 hydroxyalky, C1-C10 polyhydroxyalkyl, C1-C10 alkoxyl, C1-C10 alkoxyalkyl, —$SO_3H$, —$(CH_2)_c$$CO_2H$, and —$(CH_2)_c$$NR^9R^{10}$;

each of $R^9$ and $R^{10}$ is independently selected from hydrogen, C1-C10 alkyl, C5-C10 aryl, and C1-C10 polyhydroxyalkyl;

each of a, b, and c independently ranges from 0 to 10.

each of A and B is independently selected from —$(CH_2)_d$$Y(CH_2)_e$—, —$C(R^{11})$=$C(R^{12})$—$C(R^{13})$=$C(R^{14})$—, —N=$C(R^{12})$—$C(R^{13})$=$C(R^{14})$—, —$C(R^{11})$=N—$C(R^{13})$=$C(R^{14})$—, —$C(R^{15})$=$C(R^{12})$N=$C(R^{14})$—, —$C(R^{11})$=$C(R^{12})$—$C(R^{13})$=N—, —$C(R^{11})$=$C(R^{12})$—$N(R^{15})$—, —$C(R^{11})$=$C(R^{12})$—O—, —$C(R^{11})$=$C(R^{12})$—S—, —N=$C(R^{11})$—$N(R^{15})$—, —N=$C(R^{11})$—O—, —N—$C(R^{11})$—S—, —$C(R^{11})$=N—$N(R^{15})$—, —$C(R^{11})$=N—N$(R^{15})$—, —$C(R^{11})$=N—O—, —N=N—$N(R^{15})$—, —N=N—O— or —N=N—S—;

Y is selected from —O—, —$NR^{16}$—, —S—, —SO— or —$SO_2$—, wherein each of d and e independently varies from 0 to 3, and $R^{16}$ is selected from hydrogen, $C_1$-$C_{10}$ alkyl, $C_5$-$C_{10}$ aryl, $C_1$-$C_{10}$ hydroxyalkyl, or $C_1$-$C_{10}$ alkoxyalkyl;

wherein each of $R^5$ to $R^8$ and each of $R^{11}$ to $R^{15}$ is independently selected from hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, $C_1$-$C_{10}$ acyl, nitro, cyano, —$(CH_2)_f$$N_3$, —$(CH_2)_f$$CO_2R^{16}$, —$(CH_2)_f$$NR^{16}R^{17}$, —$NR^{16}CON_3$, —$(CH_2)_f$$CONR^{16}R^{17}$, —$(CH_2)_f$$CON_3$, —$(CH_2)_f$$SON_3$, —$(CH_2)_f$$SO_2N_3$, —$(CH_2)_f$$CON(R^{16})E2$, —$(CH_2)_f$$N(R^{16})COE2$, —$(CH_2)_f$$N(R^{16})CON(R^{17})E2$ or —$(CH_2)_f$$N(R^{16})CSN(R^{17})E2$, wherein f varies from 0 to 10 and each of $R^{16}$ and $R^{17}$ is independently selected from hydrogen, $C_1$-$C_{10}$ alkyl, $C_5$-$C_{10}$ aryl, $C_1$-$C_{10}$ hydroxyalkyl, or $C_1$-$C_{10}$ alkoxyalkyl; and each of E1 and E2 is independently hydrogen or a targeting moiety.

In some embodiments, each of E1 and E2, if present, is a whole or fragmented somatostatin receptor binding molecule, whole or fragmented ST receptor binding molecule, whole or fragmented neurotensin receptor binding molecule, whole or fragmented bombesin receptor binding molecule, whole or fragmented CCK receptor binding molecule, whole or fragmented steroid receptor binding molecule, or whole or fragmented carbohydrate receptor binding molecule.

In some embodiments, at least one of E1, $R^5$ to $R^8$, and $R^{11}$ to $R^{15}$ is a targeting moiety where at least one of $R^5$ to $R^8$ or $R^{11}$ to $R^{15}$ is selected from —$(CH_2)_f$$CON(R^{16})E2$, —$(CH_2)_f$$N(R^{16})COE2$, —$(CH_2)_f$$N(R^{16})CON(R^{17})E2$ and —$(CH_2)_f$$N(R^{16})CSN(R^{17})E2$. Further, f varies from 0 to 10, and each of $R^{16}$ and $R^{17}$ is independently selected from hydrogen, $C_1$-$C_{10}$ alkyl, $C_5$-$C_{10}$ aryl, $C_1$-$C_{10}$ hydroxyalkyl and $C_1$-$C_{10}$ alkoxyalkyl. The other substituents are as previously defined.

Synthesis of photoactivator compounds, such as azido compounds, may be accomplished by a variety of methods known in the art, such as disclosed in S. R. Sandler and W.

Kara, Azides. *In Organic Functional Group Preparations (Second Edition)*, pp. 323-349, Academic Press: New York, 1986, which is expressly incorporated by reference herein in its entirety. Aromatic azides derived from acridone, xanthone, anthraquinone, phenanthridine, and tetrafluorophenyl systems have been shown to photolyze in the visible and in UV-A regions, for example, L. K. Dyall and J. A. Ferguson, Pyrolysis of aryl azides. XI Enhanced neighbouring group effects of carbonyl in a locked conformation. *Australian Journal of Chemistry.* 1992, 45, 1991-2002; A. Y. Kolendo, Unusual product in the photolysate of 2-azidoxanthone. *Chemistry of Heterocyclic Compounds,* 1998, 34 (10), 1216; R. Theiler, Effect of infrared and visible light on 2-azidoanthraquinone in the QA binding site of photosynthetic reaction centers. An unusual mode of activation of photoaffinity label. *Biological Chemistry Hoppe-Seyler,* 1986, 367 (12), 1197-207; C. E. Cantrell and K. L. Yielding, Repair synthesis in human lymphocytes provoked by photolysis of ethidium azide. *Photochemistry and Photobiology.* 1977, 25 (2), 1889-191; and R. S. Pandurangi et al., Chemistry of bifunctional photoprobes 3: correlation between the efficiency of CH insertion by photolabile chelating agents. First example of photochemical attachment of 99 mTc complex with human serum albumin. *Journal of Organic Chemistry,* 1998, 63, 9019-9030, each of which is expressly incorporated by reference herein in its entirety. The compounds may contain additional functionalities that can be used to attach various types of biomolecules, synthetic polymers, and organized aggregates for selective delivery to various organs or tissues of interest. Examples of synthetic polymers include polyaminoacids, polyols, polyamines, polyacids, oligonucleotides, aborols, dendrimers, and aptamers.

Figure 3:
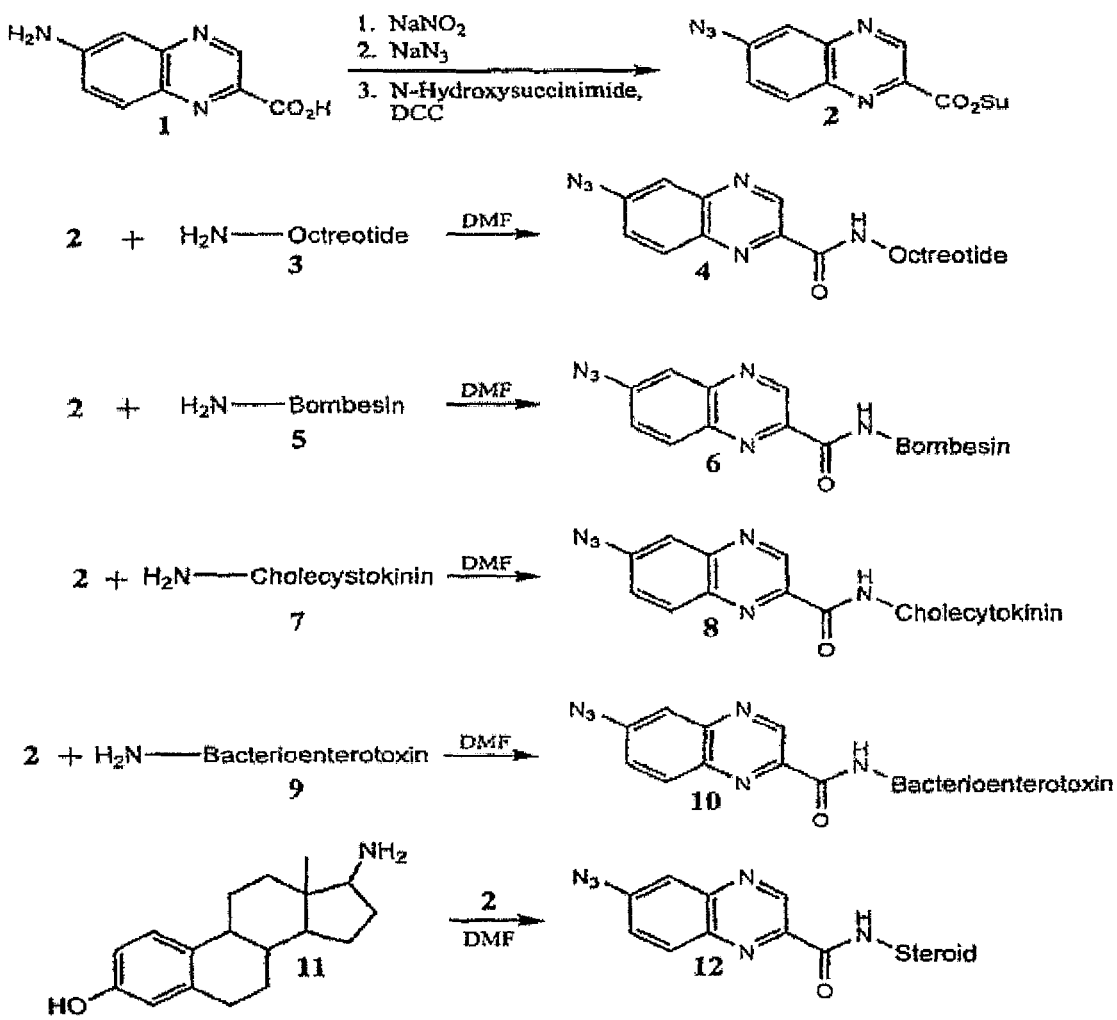
FIG. 3 is a bioconjugation scheme of the invention.

The general synthesis of compounds of the type shown in formulas I-VIII has been known for several decades, and can be readily prepared by the methods well known in the art. See: The Pyrazines. The Chemistry of Heterocyclic Compounds, G. B. Barlin, Ed., J. Wiley, New York, 1982; and The Pyrazines: Supplement 1. The Chemistry of heterocyclic compounds, D. J. Brown, Ed., J. Wiley, New York, 2002. The coupling of biomolecules such as somatostatin, bombesin, cholecystokinin, bacterioenterotoxin, steroids, and the like to compounds of formulas I-VIII can be achieved by the use of succinimido active esters, for example, as illustrated in FIG. 3.

Successful specific targeting of fluorescent dyes to tumors using antibodies and peptides for diagnostic imaging of tumors has been demonstrated by us and others as described in Achilefu et al., Novel receptor-targeted fluorescent contrast agents for in vivo imaging of tumors, *Investigative Radiology,* 2000, 35, pp. 479-485; Ballou et al., Tumor labeling in vivo using cyanine conjugated monoclonal antibodies, *Cancer Immunology and Immunotherapy,* 1995, 41, pp. 257-263; and Licha et al., New contrast agent for optical imaging: acid cleavable conjugates of cyanine dyes with biomolecules, in *Biomedical Imaging: Reporters, Dyes and Instrumentation. Proceedings of SPIE,* 1999, 3600, pp. 29-35, each of which is expressly incorporated by reference herein in its entirety. Therefore, receptor-targeted photochemicals are effective in reaching and activation at the site of various lesions.

Some exemplary methods of performing photochemical procedures using compounds including photosensitizers of formulas I-VIII encompass administering to a patient an effective amount of a compound of the invention in a biologically acceptable formulation. The compound is activated, either immediately or after allowing an interval for its accumulation at a target site, followed by illumination with light of wavelength 300 to 1200 nm, preferably 350 to 850 nm, at the site of the lesion. If the lesion is on the skin surface, or on a photo-accessible surface other than skin, such as a mucosal surface of the oral cavity, vagina, or nasal cavity, it may be directly illuminated. If the lesion is in or on a cavity, it may be illuminated with an endoscopic catheters equipped with a light source. Such an application may be used, for example, with a lesion in a blood vessel, lung, heart, throat, ear, rectum, bladder, stomach, intestines, or esophagus. For a lesion in an organ, such as liver, brain, prostate, breast, pancreas, etc., a photochemical compound in the tissue can be illuminated using a surgical instrument (forceps, scalpel, etc.) containing or configured with an illumination system. Such instruments are known to one skilled in the art, such as fiber optic instruments available from BioSpec (Moscow, 11991, Russia) for example, TC-I fiber optic tool for photodynamic therapy with fine needle tip for irradiating interstitial tumors. A surgeon performing a procedure is thus able to expose a tumor or other target tissue to light of a desired wavelength, power, and fluence rate during a procedure. The intensity, power, duration of illumination, and the wavelength of the light may vary widely depending on the location and site of the lesions. The fluence rate is preferably, but not always, kept below 200 mW/cm$^2$ to minimize thermal effects. Appropriate power depends on the size, depth, and pathology of the lesion. The inventive compounds have broad clinical utility that includes, but is not limited to, phototherapy of tumors, inflammatory processes, and impaired vasculature.

The particular wavelength(s) required for photoactivation to achieve phototherapy with a specific compound may be determined in a variety of ways. As one example, it may be determined empirically from exposing the synthesized compound to light of varying wavelength and thereafter assaying to determine the extent of tissue damage at a targeted site. It may also be determined based upon the known photoactivation maxima for the particular photosensitizer. In general, agents that act via a Type 1 mechanism can be activated across a wide wavelength spectrum from about 300 nm to about 950 nm. Thus, activation of a Type 1 component or compound may be achieved using an activation wavelength in this range.

Bioconjugation Procedures and Uses

Compounds of the invention are also useful for bioconjugation procedures and methods of using bioconjugates. Thus, the invention also discloses compounds, compositions, and bioconjugation procedures and methods of using bioconjugates described herein. A bioconjugation procedure encompasses any type of biologic procedure using the compounds disclosed herein, and includes any type of attachment of a compound of the invention to a bioactive component or targeting moiety or carrier using the compounds disclosed herein and also includes in vivo and in vitro procedures and therapeutic and diagnostic procedures. The following is a non-limiting description of various embodiments of exemplary compounds of the general formula: E1-L-Ar-X-PA (Formula IX) which are particularly useful for bioconjugation procedures and uses. It is noted that any variables in the formulas described herein, particularly with respect to Formula IX can take any definition provided in this specification, unless otherwise specified.

In embodiments, PA of Formula IX is an attachment group that contains hydrogen, $C_1$-$C_{10}$ alkyl, vinyl, ethynyl, $C_5$-$C_{10}$ aryl, hydroxyl, carboxyl, amino, mercapto, succinimido, succinimidyloxycarbonyl, cyano, isocyanato, isothiocyanato, maleimido, and azido. In embodiments, PA of Formula IX comprises a maleimido or succinimidyloxycarbonyl group. In embodiments, PA of Formula IX comprises a succinimide group. In embodiments, PA of Formula IX comprises an N—$CO_2$-succinimide group.

In embodiments, Ar in Formula IX is a pyrazine chromophore represented by Formulas I-III.

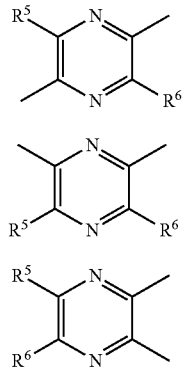

Formula I

Formula II

Formula III

In embodiments, E1, if present, may be hydrogen or a targeting moiety in Formula IX. In embodiments, E1 is hydrogen in Formula IX.

In embodiments, provided is a compound of the formula: E1-L-Ar-X-PA (Formula IX), wherein:

Ar is

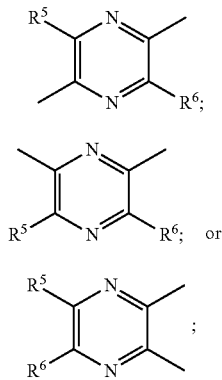

Formula 1

Formula II

Formula III

E1 is hydrogen or a targeting moiety; X is selected from a single bond, —(CH$_2$)$_a$—, —CO—, —OCO—, —HNCO—, —(CH$_2$)$_a$CO—, —(CH$_2$)$_a$OCO—, C$_1$-C$_{10}$ alkyl, C$_5$-C$_{10}$ aryl, C$_5$-C$_{10}$ heteroaryl, C$_1$-C$_{10}$ acyl, nitro, cyano, —(CH$_2$)$_a$CO$_2$—, —(CH$_2$)$_a$NR$^1$—, —NR$^1$CO—, —(CH$_2$)$_a$CONR$^1$—, —(CH$_2$)$_a$SO—, —(CH$_2$)$_a$SO$_2$—, —(CH$_2$)$_a$CON(R$^1$)—, —(CH$_2$)$_a$N(R$^1$)CO—, —(CH$_2$)$_a$N(R$^1$)CON(R$^2$)— and —(CH$_2$)$_a$N(R$^1$)CSN(R$^2$)—;

L is selected from a single bond, —HNCO—, —CONR$^3$—, —(CH$_2$)$_b$—, —(CH$_2$)$_b$CONR$^3$—, —N(R$^3$)CO(CH$_2$)$_b$—, —OCO(CH$_2$)$_b$—, —(CH$_2$)$_b$CO$_2$—, —OCONH—, —OCO$_2$—, —HNCONH—, —HNCSNH—, —HNNHCO—, —OSO$_2$—, —NR$^3$(CH$_2$)$_b$CONR$^4$—, —CONR$^3$(CH$_2$)$_b$NR$^4$CO—, —NR$^3$CO(CH$_2$)$_b$CONR$^4$—, —(CH$_2$)$_b$CON(R$^3$)—, —(CH$_2$)$_b$N(R$^3$)CO—, —(CH$_2$)$_b$N(R$^3$)CON(R$^4$)— and —(CH$_2$)$_b$N(R$^3$)CSN(R$^4$)—;

PA is —OZ or —NR$^9$Z; Z is selected from —(CH$_2$)$_c$CO$_2$H, —(CH$_2$)$_c$NR$^9$R$^{10}$, —(CH$_2$)$_c$NCO, —(CH$_2$)$_c$NCS, (CH$_2$)$_c$OH, —(CH$_2$)$_c$SH, —(CH$_2$)$_c$C≡CH, —(CH$_2$)$_c$C≡N, —(CH$_2$)$_c$N$_3$,

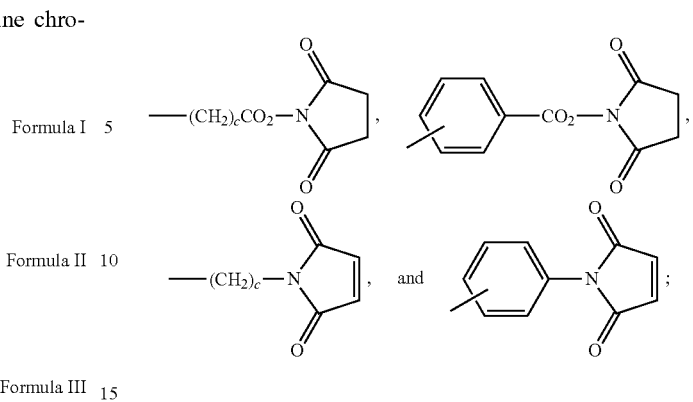

each of R$^1$, R$^2$, R$^3$ and R$^4$ is independently selected from hydrogen, C1-C10 alkyl, —OH, C5-C10 aryl, C1-C10 hydroxyalky, C1-C10 polyhydroxyalkyl, C1-C10 alkoxyl, C1-C10 alkoxyalkyl, —(CH$_2$)$_c$CO$_2$H, and —(CH$_2$)$_c$NR$^9$R$^{10}$; R$^5$ and R$^6$ are each independently —(CH$_2$)$_f$NR$^{16}$R$^{17}$; R$^9$ and R$^{10}$ are each independently selected from hydrogen, C1-C10 alkyl, C5-C10 aryl, and C1-C10 maleimidoalkylcarbonyl; R$^{16}$ and R$^{17}$ are each independently hydrogen, C$_1$-C$_{10}$ alkyl, C$_5$-C$_{10}$ aryl, C$_1$-C$_{10}$ hydroxyalkyl, and C$_1$-C$_{10}$ alkoxyalkyl; each a is an integer independently selected from 0 to 10; each b is an integer independently selected from 0 to 10; each c is an integer independently selected from 0 to 10; and each f is an integer independently selected from 0 to 10. In an embodiment, provided is the compound of Formula IX wherein f is 0. In an embodiment, provided is the compound of Formula IX wherein PA is —NR$^9$Z. In an embodiment, provided is the compound of Formula IX wherein R$^{16}$ is hydrogen or C1-C10 alkyl. In an embodiment, provided is the compound of Formula IX wherein L is —CONR$^3$— and R$^3$ is C1-C10 alkoxyalkyl, —(CH$_2$)$_c$CO$_2$H, or —(CH$_2$)$_c$NR$^9$R$^{10}$. In an embodiment, provided is the compound of Formula IX wherein R$^3$ is C1-C10 alkoxyalkyl.

In an embodiment, provided is the compound of Formula IX wherein Z is

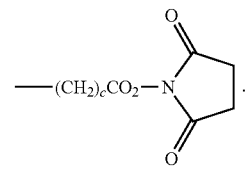

In an embodiment, provided is the compound of Formula IX wherein Z is

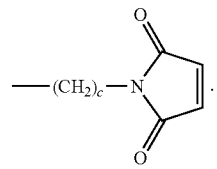

In an embodiment, provided is the compound of Formula IX wherein Z is —(CH$_2$)$_c$CO$_2$H. In an embodiment, provided is the compound of Formula IX wherein R$^3$ is —(CH$_2$)$_c$NR$^9$R$^{10}$. In an embodiment, provided is the compound of Formula IX wherein Z is —(CH$_2$)$_c$NR$^9$R$^{10}$. In an embodiment, provided is the compound of Formula IX wherein R$^9$ and $R^{10}$ are both hydrogen. In an embodiment, provided is the compound of Formula IX wherein Z is selected from:

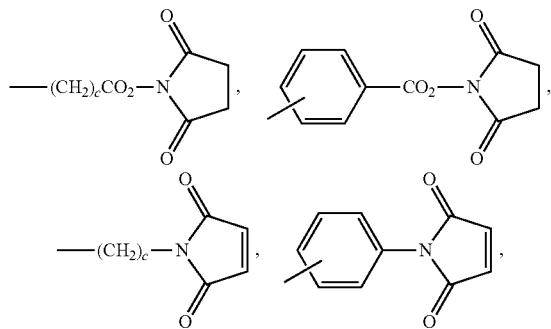

or —$(CH_2)_c NR^9 R^{10}$ where $R^9$ or $R^{10}$ is C1-C10 maleimidoalkylcarbonyl.

In an embodiment, provided is the compound of Formula IX wherein: E1 is hydrogen; X is —CO—; L is —CONR³—; PA is —OZ or —NHZ; Z is selected from the group consisting of —$(CH_2)_c CO_2 H$, —$(CH_2)_c NR^9 R^{10}$, —$(CH_2)_c NCO$, —$(CH_2)_c NCS$, —$(CH_2)_c OH$, —$(CH_2)_c SH$, —$(CH_2)_c C≡CH$, —$(CH_2)_c C≡N$, —$(CH_2)_c N_3$,

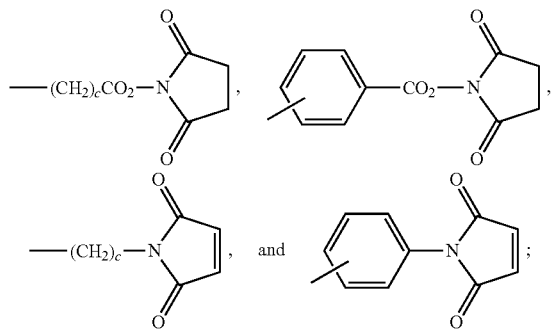

$R^3$ is selected from the group consisting of hydrogen, C1-C10 alkyl, —OH, C5-C10 aryl, C1-C10 hydroxyalky, C1-C10 polyhydroxyalkyl, C1-C10 alkoxyl, C1-C10 alkoxyalkyl, —$(CH_2)_c CO_2 H$, and —$(CH_2)_c NR^9 R^{10}$; $R^5$ and $R^6$ are each independently —$(CH_2)_f NR^{16} R^{17}$; $R^9$ and $R^{10}$ are each independently selected from the group consisting of hydrogen, C1-C10 alkyl, C5-C10 aryl, and C1-C10 maleimidoalkylcarbonyl; $R^{16}$ and $R^{17}$ are each independently selected from the group consisting of hydrogen, $C_1$-$C_{10}$ alkyl, $C_5$-$C_{10}$ aryl, $C_1$-$C_{10}$ hydroxyalkyl, and $C_1$-$C_{10}$ alkoxyalkyl; each c is an integer independently selected from 0 to 10; and f is 0.

Also provided are compounds and methods of using compounds of general Formula IX which are attached to a biomolecule. In an embodiment, provided is the compound of E1-L-Ar-X-PA (Formula IX), wherein:

Ar is

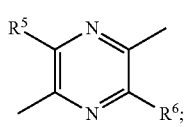

Formula 1

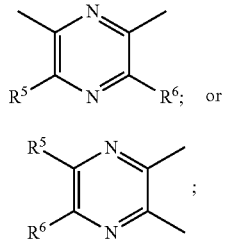

E1 is hydrogen or a targeting moiety; X is selected from a single bond, —$(CH_2)_a$—, —CO—, —OCO—, —HNCO—, —$(CH_2)_a CO$—, —$(CH_2)_a OCO$—, $C_1$-$C_{10}$ alkyl, $C_5$-$C_{10}$ aryl, $C_5$-$C_{10}$ heteroaryl, $C_1$-$C_{10}$ acyl, nitro, cyano, —$(CH_2)_a CO_2$—, —$(CH_2)_a NR^1$—, —$NR^1 CO$—, —$(CH_2)_a CONR^1$—, —$(CH_2)_a SO$—, —$(CH_2)_a SO_2$—, —$(CH_2)_a CON(R^1)$—, —$(CH_2)_a N(R^1)CO$—, —$(CH_2)_a N(R^1)CON(R^2)$— and —$(CH_2)_a N(R^1)CSN(R^2)$—; L is selected from a single bond, —HNCO—, —CONR³—, —$(CH_2)_b$—, —$(CH_2)_b CONR^3$—, —$N(R^3)CO(CH_2)_b$—, —$OCO(CH_2)_b$—, —$(CH_2)_b CO_2$—, —OCONH—, —$OCO_2$—, —HNCONH—, —HNCSNH—, —HNNHCO—, —$OSO_2$—, —$NR^3(CH_2)_b CONR^4$—, —$CONR^3(CH_2)_b NR^4 CO$—, —$NR^3 CO(CH_2)_b CONR^4$—, —$(CH_2)_b CON(R^3)$—, —$(CH_2)_b N(R^3)CO$—, —$(CH_2)_b N(R^3)CON(R^4)$— and —$(CH_2)_b N(R^3)CSN(R^4)$—; PA is —OZ' or —$NR^9 Z'$; Z' is selected from —$(CH_2)_c CO_2$-CARRIER, —$(CH_2)_c NR^9$-CARRIER, —$(CH_2)_c NCO$-CARRIER, —$(CH_2)_c O$-CARRIER, —$(CH_2)_c$-CARRIER, —$(CH_2)_c$—CO-CARRIER, each $R^1$, $R^2$, $R^3$ and $R^4$ is independently selected from hydrogen, C1-C10 alkyl, —OH, C5-C10 aryl, C1-C10 hydroxyalky, C1-C10 polyhydroxyalkyl, C1-C10 alkoxyl, C1-C10 alkoxyalkyl, —$(CH_2)_c CO_2 H$, and —$(CH_2)_c NR^9 R^{10}$; $R^5$ and $R^6$ are each independently —$(CH_2)_f NR^{16} R^{17}$; $R^9$ and $R^{10}$ are each independently selected from the group consisting of hydrogen, C1-C10 alkyl, C5-C10 aryl, and C1-C10 maleimidoalkylcarbonyl; $R^{16}$ and $R^{17}$ are each independently selected from hydrogen, $C_1$-$C_{10}$ alkyl, $C_5$-$C_{10}$ aryl, $C_1$-$C_{10}$ hydroxyalkyl, or $C_1$-$C_{10}$ alkoxyalkyl; each a is an integer independently selected from 0 to 10; each b is an integer independently selected from 0 to 10; each c is an integer independently selected from 0 to 10; and each f is an integer independently selected from 0 to 10. In an embodiment, CARRIER is a targeting moiety selected from a whole or fragmented receptor binding molecule, a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented cholecystekinin (CCK) receptor binding molecule, a whole or fragmented steroid receptor binding molecule, or a whole or fragmented carbohydrate receptor binding molecule. In an aspect of this embodiment, provided is a compound of Formula IX which is attached to a peptide, protein, antibody, aptamer or polymer. In an aspect of this embodiment, provided is a compound of Formula IX which is attached to a targeting moiety selected from a receptor binding molecule, a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented cholecystekinin (CCK) receptor binding molecule, a whole or fragmented steroid receptor binding molecule, or a whole or fragmented carbohydrate receptor binding molecule.

Also provided is a method of using a compound in an optical imaging, diagnostic, monitoring or therapeutic biomedical procedure, comprising: administering a compound of Formula IX attached to a carrier to a patient; exposing the administered compound to visible and/or near infrared light.

Also provided is a method of making a targeted compound comprising: contacting a compound of formula: E1-L-Ar-X-PA (Formula IX), wherein:

Ar is

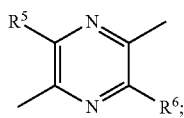

Formula I

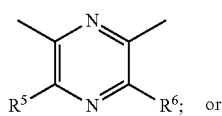

Formula II

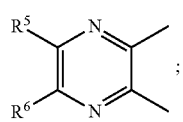

Formula III

E1 is hydrogen or a targeting moiety;

X is selected from a single bond, —(CH$_2$)$_a$—, —CO—, —OCO—, —HNCO—, —(CH$_2$)$_a$CO—, —(CH$_2$)$_a$OCO—, C$_1$-C$_{10}$ alkyl, C$_5$-C$_{10}$ aryl, C$_5$-C$_{10}$ heteroaryl, C$_1$-C$_{10}$ acyl, nitro, cyano, —(CH$_2$)$_a$CO$_2$—, —(CH$_2$)$_a$NR$^1$—, —NR$^1$CO—, —(CH$_2$)$_a$CONR$^1$—, —(CH$_2$)$_a$SO, —(CH$_2$)$_a$SO$_2$—, —(CH$_2$)$_a$CON(R$^1$)—, —(CH$_2$)$_a$N(R$^1$)CO—, —(CH$_2$)$_a$N(R$^1$)CON(R$^2$)— and —(CH$_2$)$_a$N(R$^1$)CSN(R$^2$)—;

L is selected from a single bond, —HNCO—, —CONR$^3$, —(CH$_2$)$_b$—, —(CH$_2$)$_b$CONR$^3$—, —N(R$^3$)CO(CH$_2$)$_b$—, —OCO(CH$_2$)$_b$—, —(CH$_2$)$_b$CO$_2$—, —OCONH—, —OCO$_2$—, —HNCONH—, —HNCSNH—, —HNNHCO—, —OSO$_2$—, —NR$^3$(CH$_2$)$_b$CONR$^4$—, —CONR$^3$(CH$_2$)$_b$NR$^4$CO—, —NR$^3$CO(CH$_2$)$_b$CONR$^4$—, —(CH$_2$)$_b$CON(R$^3$)—, —(CH$_2$)$_b$N(R$^3$)CO—, —(CH$_2$)$_b$N(R$^3$)CON(R$^4$)— and —(CH$_2$)$_b$N(R$^3$)CSN(R$^4$)—;

PA is —OZ or —NR$^9$Z;

Z is selected from —(CH$_2$)$_c$CO$_2$H, —(CH$_2$)$_c$NR$^9$R$^{10}$, —(CH$_2$)$_c$NCO, —(CH$_2$)$_c$NCS, —(CH$_2$)$_c$OH, —(CH$_2$)$_c$SH, —(CH$_2$)$_c$C≡CH, —(CH$_2$)$_c$C≡N, —(CH$_2$)$_c$N$_3$,

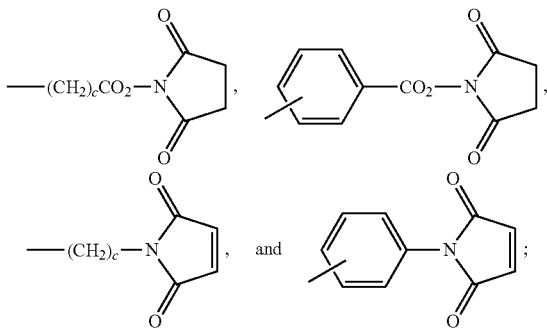

each R$^1$, R$^2$, R$^3$, and R$^4$ is independently selected from hydrogen, C1-C10 alkyl, —OH, C5-C10 aryl, C1-C10 hydroxyalky, C1-C10 poly hydroxyalkyl, C1-C10 alkoxyl, C1-C10 alkoxyalkyl, —(CH$_2$)$_c$CO$_2$H, and —(CH$_2$)$_c$NR$^9$R$^{10}$;

R$^5$ and R$^6$ are each independently —(CH$_2$)$_f$NR$^{16}$R$^{17}$;

R$^9$ and R$^{10}$ are each independently selected from hydrogen, C1-C10 alkyl, C5-C10 aryl, and C1-C10 maleimidoalkylcarbonyl;

R$^{16}$ and R$^{17}$ are each independently hydrogen, C$_1$-C$_{10}$ alkyl, C$_5$-C$_{10}$ aryl, C$_1$-C$_{10}$ hydroxyalkyl, and C$_1$-C$_{10}$ alkoxyalkyl;

each a is an integer independently selected from 0 to 10;
each b is an integer independently selected from 0 to 10;
each c is an integer independently selected from 0 to 10; and
each f is an integer independently selected from 0 to 10;

with a coupling agent and a CARRIER compound comprising a targeting moiety selected from a whole or fragmented receptor binding molecule, a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented cholecystekinin (CCK) receptor binding molecule, a whole or fragmented steroid receptor binding molecule, or a whole or fragmented carbohydrate receptor binding molecule.

In an embodiment, the coupling agent is selected from DCC, EDC, i-BuOCOCl, EDC/HOBt, PyBOP, PyBrOP, HATU, HBTU and other agents known in the art.

Also provided is a compound of Formula IX and a pharmaceutically acceptable carrier.

When the phrase "single bond" is used, the variable is not present and there is a direct bond between the substituents which are present. For example, in Formula IX, if variable X is a single bond, there is direct coupling of Ar and PA.

In a particular embodiment of the compounds of Formula IX, X is —CO—; L is —CONR$^3$—; PA is —OZ or —NHZ; Z is selected from the group consisting of —(CH$_2$)$_c$CO$_2$H, —(CH$_2$)$_c$NR$^9$R$^{10}$, —(CH$_2$)$_c$NCO, —(CH$_2$)$_c$NCS, —(CH$_2$)$_c$OH, —(CH$_2$)$_c$SH, —(CH$_2$)$_c$C≡CH, —(CH$_2$)$_c$C≡N, —(CH$_2$)$_c$N$_3$,

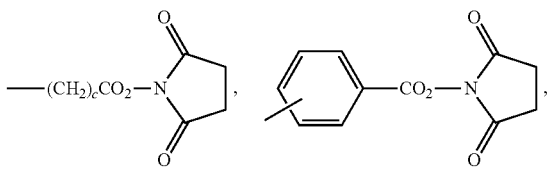

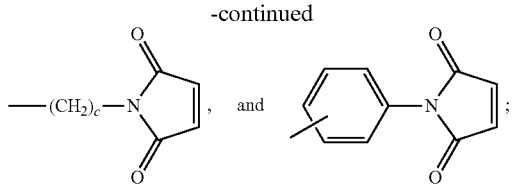

In separate embodiments, each of a to f is independently an integer from 0 to 10.

In separate embodiments of the compounds of Formula IX, $R^3$ is selected from the group consisting of hydrogen, C1-C10 alkyl, —OH, C5-C10 aryl, C1-C10 hydroxyalky, C1-C10 polyhydroxyalkyl, C1-C10 alkoxyl, C1-C10 alkoxyalkyl, —(CH$_2$)$_c$CO$_2$H, and —(CH$_2$)$_c$NR$^9$R$^{10}$; $R^5$ and $R^6$ are each independently —(CH$_2$)$_f$NR$^{16}$R$^{17}$; $R^9$ and $R^{10}$ are each independently selected from the group consisting of hydrogen, C1-C10 alkyl, C5-C10 aryl, and C1-C10 maleimidoalkylcarbonyl; $R^{16}$ and $R^{17}$ are each independently selected from hydrogen, $C_1$-$C_{10}$ alkyl, $C_5$-$C_{10}$ aryl, $C_1$-$C_{10}$ hydroxyalkyl, or $C_1$-$C_{10}$ alkoxyalkyl.

Again, a targeting moiety generally refers to a particular region of the compound that is recognized by, and binds to, a target cell, tissue, organ, etc. A targeting moiety may include an antibody (all or a portion, and monoclonal or polyclonal), peptide, peptidomimetic, carbohydrate, glycomimetic, drug, hormone, nucleic acid, lipid, albumin, receptor binding molecule, inclusion compound (a compound that has a cavity with a defined volume such that it can incorporate small molecules or a part of a small molecule) such as cyclodextrins (cyclodextrins can accommodate hydrophobic residues such as adamantine, benzene, etc), etc.

Targeting moieties may be part of a biomolecule which include hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. Specific examples of targeting moieties include steroid hormones for the treatment of breast and prostate lesions, whole or fragmented somatostatin, bombesin, and neurotensin receptor binding molecules for the treatment of neuroendocrine tumors, whole or fragmented cholecystekinin receptor binding molecules for the treatment of lung cancer, whole or fragmented heat sensitive bacterioendotoxin (ST) receptor and carcinoembryonic antigen (CEA) binding molecules for the treatment of colorectal cancer, dihyroxyindolecarboxylic acid and other melanin producing biosynthetic intermediates for melanoma, whole or fragmented integrin receptor and atherosclerotic plaque binding molecules for the treatment of vascular diseases, and whole or fragmented amyloid plaque binding molecules for the treatment of brain lesions. In some embodiments, a targeting moiety is selected from octreotide and octreotate peptides, heat-sensitive bacterioendotoxin receptor binding peptide, carcinoembryonic antigen antibody (anti-CEA), bombesin receptor binding peptide, neurotensin receptor binding peptide, cholecystekinin receptor binding peptide, or estrogen.

As a non-limiting example, and with respect to compounds that may be used as targeting moieties because they bind to a receptor, one skilled in the art would appreciate that diethylstilbesterol is not a steroid but strongly binds to the estrogen receptor (a steroid receptor); testosterone does not bind to the estrogen receptor, testosterone and esterone do not bind to the corticosteroid receptors, cortisone and aldosterone do not bind to the sex hormone receptors, and the following compounds are known to bind to the estrogen receptor, namely, estratriol, 17β-aminoestrogen (AE) derivatives such as prolame and butolame, drugs such as tamoxifen, ICI-164384, raloxifene, genistein, 17β-estradiol, glucocorticoids, progesterone, estrogens, retinoids, fatty acid derivatives, phytoestrogens, etc. Thus, one skilled in the art would know how to select compounds to target and/or to avoid a particular site.

For targeting purposes, an external attachment of a targeting moiety is usually desirable unless the compounds themselves preferentially accumulate in the target tissue, thereby obviating the need for an additional binding group. For example, administering delta-aminolevulinic acid, an intermediate in porphyrin biosynthesis, results in a two-fold uptake of porphyrins in tumors compared to normal tissues. Similarly, administering dihydroxyindole-2-carboxylic acid, an intermediate in melanin biosynthesis, produces substantially enhanced levels of melanin in melanoma cells compared to normal cells. Thus, an inventive compound may be delivered to the site of a lesion by attaching it to these types of biosynthetic intermediates. Although this targeting is less specific than in embodiments where a specific targeting moiety is included in the compound, it still targets the compound to a desired site and thus is another embodiment of the invention.

Compounds of the invention may be used in compositions and in vitro or in vivo biological procedures. Conjugation of a small molecule to a small peptide or other small molecule carrier generally preserves receptor binding capability. Coupling of diagnostic and radiotherapeutic agents to biomolecules can be accomplished by methods well known in the art, as disclosed in Hnatowich et al., Radiolabeling of Antibodies: A simple and efficient method. *Science*, 1983, 220, 613; A. Pelegrin et al., Photoimmunodiagnostics with antibody-fluorescein conjugates: in vitro and in vivo preclinical studies. *Journal of Cellular Pharmacology.* 1992, 3, 141-145, and U.S. Pat. No. 5,714,342, which are expressly incorporated by reference herein in their entirety.

Formulas I-III in Formula IX are members of a class of small molecules that possess desirable absorption and emission properties in the UV-A, visible and NIR region of the electromagnetic spectrum. Various substituents such as electron donating groups, electron withdrawing groups, lipophilic groups, or hydrophilic groups can be attached at the respective carbon atoms for altering physicochemical and/or biological properties, as known to one skilled in the art. The substituents may also optionally include E1 which, when E1 is a targeting moiety, can selectively bind to a desired target tissue or lesion which may be the same or different than other targeting moieties in the molecule. The target may be a biological receptor, an enzyme, etc.

An exemplary synthesis of pyrazine derivatives of Formula IX useful as starting materials for forming bioconjugates is outlined in Scheme 1 and described in Examples 2-7.

Scheme 1
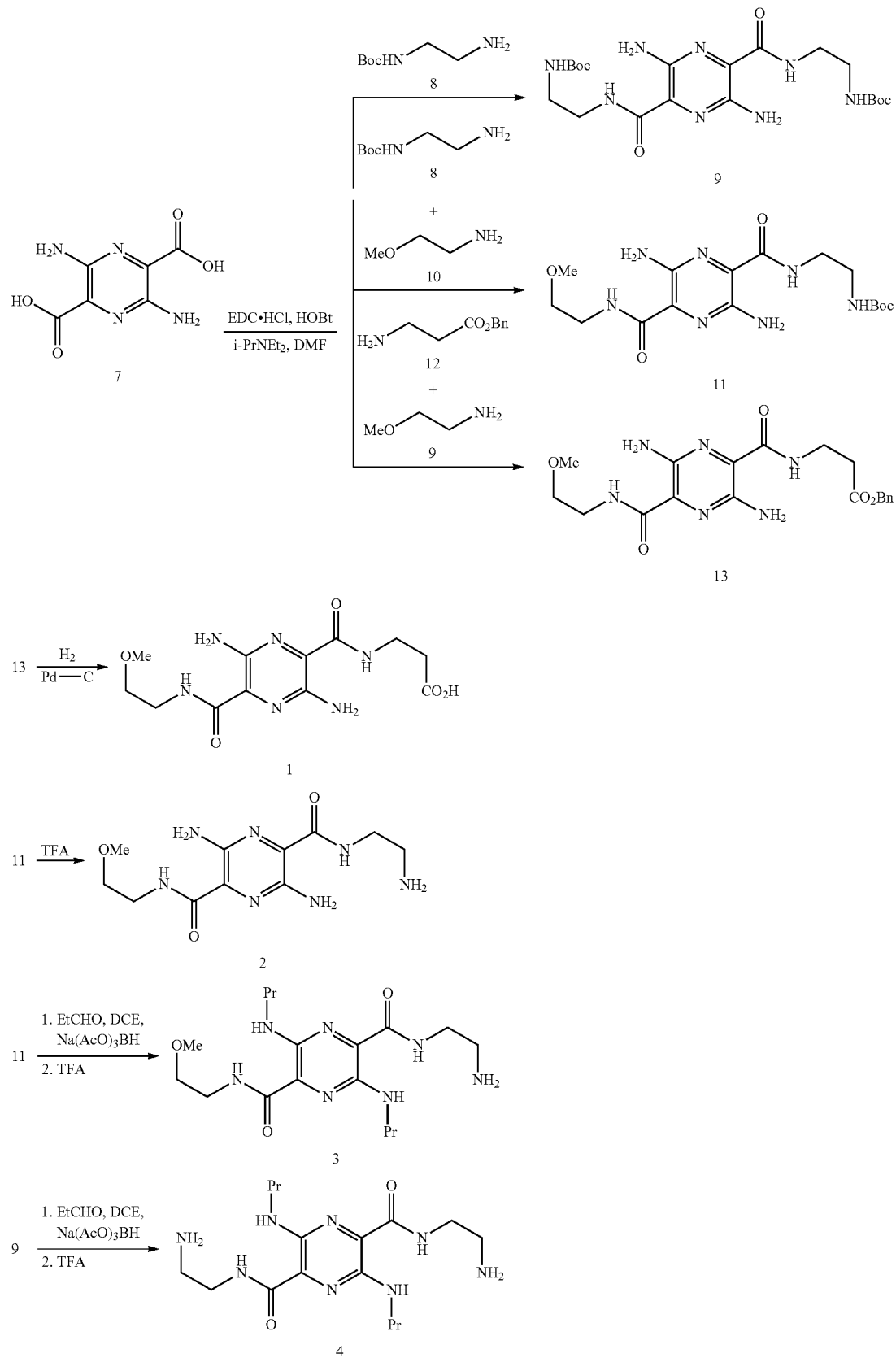

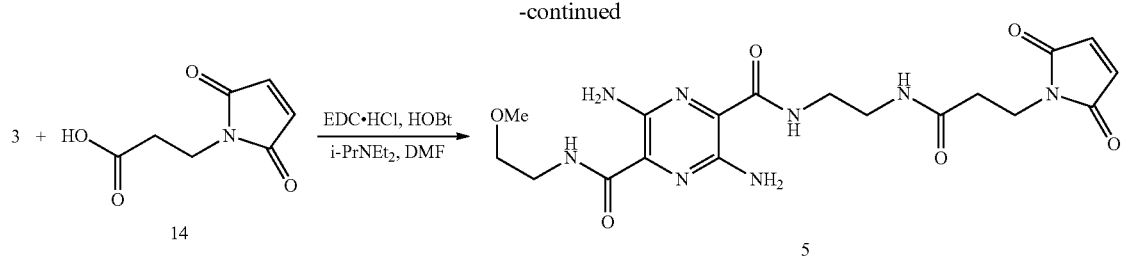

It should be noted that the same methodology is applicable for the synthesis of pyrazine derivatives of Ar formulas II and III. The compounds for Ar formulas I-III contain functionalities that can be used to attach various types of biomolecules, synthetic polymers, and organized aggregates for selective delivery to various organs or tissues of interest. Examples of synthetic polymers include polyaminoacids, polyols, polyamines, polyacids, oligonucleotides, aborols, dendrimers, and aptamers.

Compounds of the invention may be used in compositions and in vitro or in vivo bioconjugation procedures. The method of attaching various haptens such as compounds having Ar formulas I-III to carriers as is well known in the art as described by Hermanson in Bioconjugate Techniques [8], which is incorporated by reference in its entirety. The coupling of biomolecules such as somatostatin, bombesin, cholecystokinin, bacterioenterotoxin, steroids, and the like to compounds of Ar formulas I-III can be achieved by the use of active esters, maleimides, and the like, as illustrated in Scheme 2.

Scheme 2

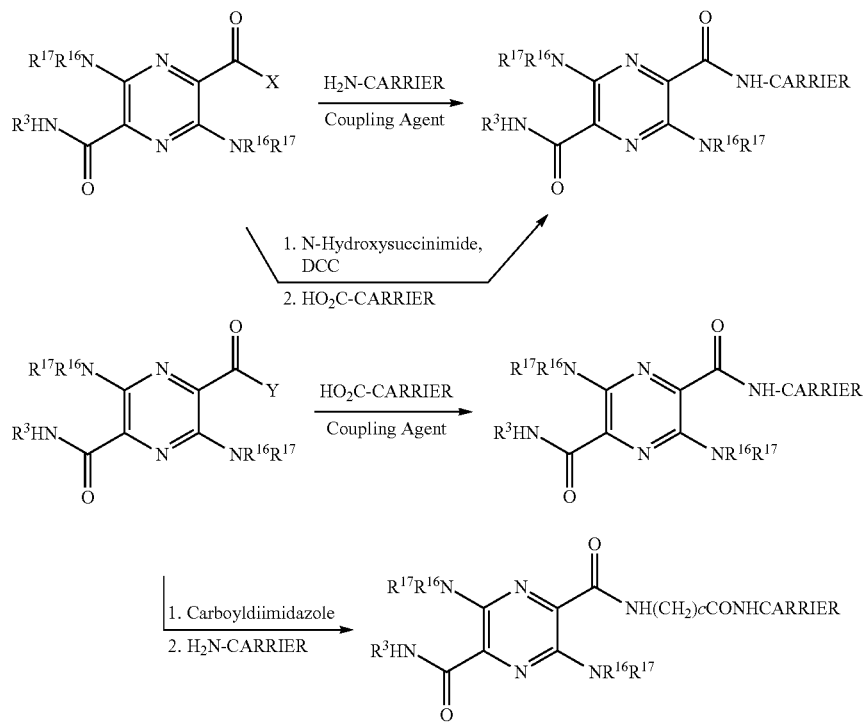

It is noted that the synthesis in Scheme 2 is exemplary. Other methods of synthesizing bioconjugates may be used, as known in the art and described herein. Successful bioconjugation of fluorescent dyes to antibodies and peptides and subsequent targeting of said bioconjugates to tumors has been demonstrated in references 9-11.

Ar Formulas I-III are members of a class of small molecules that possess desirable absorption and emission properties in the visible region of the electromagnetic spectrum. Various substituents such as electron donating groups, electron withdrawing groups, lipophilic groups, or hydrophilic groups can be attached at the respective carbon atoms for altering physicochemical and/or biological properties, as known to one skilled in the art. The compound of the general formulas may further comprise an electron donating group, an electron withdrawing group, a lipophilic group, and/or a hydrophilic group.

In some embodiments, compounds of Formula IX are attached to a biomolecule including a whole or fragmented somatostatin receptor binding molecule, whole or fragmented ST receptor binding molecule, whole or fragmented neurotensin receptor binding molecule, whole or fragmented bombesin receptor binding molecule, whole or fragmented CCK receptor binding molecule, whole or fragmented steroid receptor binding molecule, or whole or fragmented carbohydrate receptor binding molecule. As used herein, the terms "biomolecule", "bioactive molecule", "bioactive component", "targeting moiety", "bioactive carrier" and "CARRIER" and other forms of these words and phrases are all used interchangeably. The use of these terms does not necessarily the presence of a valence-satisfied compound, but rather, as is known in the art, can be a fragment or group which can attach to a portion of another molecule or molecule fragment, such as a compound of Formula IX or portion thereof.

In one example, the targeting moiety of the inventive compound may contain all or part of a steroid hormone or a steroid receptor binding compound, and therefore target steroid hormone sensitive receptors. In this example, the compound is administered, targets the desired site such as a lesion of the breast and/or prostate, is photoactivated, and forms free radicals at this site thereby effecting cell injury or death at the desired target site. Similar target binding compounds and uses will be recognized by one skilled in the art. For example, the targeting moiety may be a compound that targets and binds to a somatostatin, bombesin, CCK, and/or neurotensin receptor binding molecule, or may be a carcinogenic embryonic antigen-binding compound that binds to a carcinogenic embryonic antigen. These are then photoactivated for treatment of, for example, lung cancer cells with CCK receptor binding compounds, colorectal cancer cells with ST receptor and carcinoembryonic antigen (CEA) binding compounds, melanoma cells with dihyroxyindolecarboxylic acid, vascular sites of atherosclerotic plaque with integrin receptor binding compounds, brain lesions with amyloid plaque binding molecules, etc.

Formulations

Exemplary compositions of the invention can be formulated for enteral (oral or rectal), parenteral, topical, or cutaneous administration. A formulation may be prepared using any of the compounds previously described, along with excipients, buffers, etc., to provide a composition for administration by any one of a variety of routes. Compositions of the invention may be injected, ingested, applied topically, transdermally, subcutaneously, administered by aerosol formulation and/or inhalation, etc. After administration, a composition accumulates, for example, at a target tissue if a targeting moiety is included in the compound. The selected target site, or a site requiring diagnosis or treatment, is exposed to light with a sufficient power and fluence rate to render a diagnosis and/or treatment. Topical or cutaneous delivery may include aerosols, creams, gels, solutions, etc. Compositions of the invention are administered in doses effective to achieve the desired objective. Such doses may vary widely depending upon the particular complex employed, the organs or tissues to be examined, the equipment employed in the clinical procedure, the efficacy of the treatment achieved, and the like. Compositions of the invention can contain an effective amount of the phototherapeutic agent along with conventional pharmaceutical carriers and excipients appropriate for the type of administration contemplated. Such compositions may include stabilizing agents and skin penetration enhancing agents and/or also contain pharmaceutically acceptable buffers, emulsifiers, surfactants, and, optionally, electrolytes such as sodium chloride.

Formulations for enteral administration may vary widely as is well known in the art. In general, such formulations are liquids, which include an effective amount of the composition in an aqueous solution or suspension. Such enteral compositions may optionally include buffers, surfactants, emulsifiers, thixotropic agents, and/or the like. Compositions for oral administration may also contain flavoring agents and other ingredients for enhancing their organoleptic qualities. A topical application can be formulated as a liquid solution, water/oil emulsion, or suspension of particles, depending on the particular nature of the agent and the type of tissue to be targeted. The compositions may also be delivered in an aerosol spray.

If an inventive compound is water soluble, for example, a solution in water may be applied to or into the target tissue. Delivery into and through the skin may be enhanced by using well known methods and agents such as transdermal permeation enhancers, for example, "azone", N-alkylcyclic amides, dimethylsulfoxide, long-chained aliphatic acids ($C_{10}$), etc. if an inventive compound is not water soluble, it may be dissolved in a biocompatible oil (e.g. soybean oil, fish oil, vitamin E, linseed oil, vegetable oil, glyceride esters, and/or long-chained fatty esters) and emulsified with surface-active compounds (e.g. vegetable or animal phospholipids; lecithin; long-chained fatty salts and alcohols; Pluronics: polyethylene glycol esters and ethers; etc.) in water to make a topical cream, suspension, water/oil emulsion, water/oil microemulsion, or liposomal suspension to be delivered or applied to the target region. In the case of liposomes, an inventive compound may be attached to or be contained in the lamellar material.

The dose of compound may vary from about 0.1 mg/kg body weight to about 500 mg/kg body weight. In one embodiment, the dose is in the range of about 0.5 mg/kg body weight to about 2 mg/kg body weight. As one example, for compositions administered parenterally, a sterile aqueous solution or suspension of compound may be present in a concentration ranging from about 1 nM to about 0.5 M, typically in a concentration from about 1 µM to about 10 mM.

In general, a formulated compound including at least one photosensitizer of Formulas I-VIII is administered at a dose or in a concentration that is effective, upon exposure to light, to generate radicals at a target tissue such that cells at the target tissue are injured or killed. The target tissue is exposed for a period of time to light of a wavelength that is effective to activate the compound that produces Type 1 destruction in the target tissue. In the case of ex vivo or in vitro use (e.g., tissue culture), a formulated compound including at least one photosensitizer of Formulas I-VIII is administered at a dose or in a concentration that is effective, upon exposure to light, to generate radicals within a biological medium (e.g., culture medium or organ preservation fluid) such that target tissue in the biological medium are injured or killed. The biological medium is exposed for a period of time to light of a wavelength that is effective to activate the compound that produces Type 1 destruction in the target tissue.

The concentration of an inventive compound at the target tissue is the outcome of either passive or active uptake processes in the tissue. An example of passive uptake would be where the compound is attached or is contained within a particulate carrier. If the carrier is of an appropriate size, in the range of about 100 nm to about 1000 nm, it will leak into the perfusion boundary of vascular tumors. An example of active uptake would be where a receptor based attachment binds a particular receptor that is expressed on the target tissue. The effective concentration of a compound of the invention thus depends on the nature of the formulation, method of delivery, target tissue, activation method and toxicity to the surrounding normal tissue. Formulations for topical delivery may also contain liquid or semisolid excipients to assist in the penetration of the photosensitizer.

In some embodiments, compositions of the invention may be formulated as micelles, liposomes, microcapsules, microparticles, nanocapsules, nanoparticles, or the like. These formulations may enhance delivery, localization, target specificity, administration, etc. As one example, a liposome formulation of an inventive compound may be beneficial when the compound does not contain a specific targeting moiety (e.g., when E is hydrogen). As another example, a liposome formulation of an inventive compound may be beneficial when the compound has solubility limitations. Preparation and loading of these are well known in the art.

As one example, liposomes may be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, *Liposome Dermatics*, Springer-Verlag, Berlin (1992)). Polycaprolactone, poly(glycolic) acid, poly(lactic) acid, polyanhydride or lipids may be formulated as microspheres. As an illustrative example, the optical agent may be mixed with polyvinyl alcohol (PVA), the mixture then dried and coated with ethylene vinyl acetate, then cooled again with PVA. In a liposome, the optical agent may be within one or both lipid bilayers, in the aqueous between the bilayers, or with the center or core. Liposomes may be modified with other molecules and lipids to form a cationic liposome. Liposomes may also be modified with lipids to render their surface more hydrophilic which increases their circulation time in the bloodstream. The thus-modified liposome has been termed a "stealth" liposome, or a long-lived liposome, as described in U.S. Pat. Nos. 6,277,403; 6,610,322; 5,631,018; 5,395,619; and 6,258,378, each of which is expressly incorporated by reference herein in its entirety, and in *Stealth Liposomes*, Lasic and Martin (Eds.) 1995, CRC Press, London, specifically pages 1-6, 13-62, 93-126, 139-148, 197-210, and 233-244. Encapsulation methods include detergent dialysis, freeze drying, film forming, injection, as known to one skilled in the art and disclosed in, for example, U.S. Pat. No. 6,406,713 which is expressly incorporated by reference herein in its entirety.

A compound including at least one photosensitizer of Formulas I-VIII formulated in liposomes, microcapsules, etc. may be administered by any of the routes previously described. In a formulation applied topically, the optical agent may be slowly released over time. In an injectable formulation, the liposome capsule may circulate in the bloodstream and to be delivered to a desired site. The use of liposomes, microcapsules, or other microparticles allows the incorporation of two or more inventive compounds of different types and capabilities in a single, inventive composition.

A compound of the invention containing at least one photosensitizer of Formulas I-VIII could be also used as an antimicrobial agent and used for the treatment of infections, wounds, and/or burn healing, as described by Hamblin et al., in "Targeted photodynamic therapy for infected wounds in mice" in *Optical Methods for Tumor Treatment and Detection: Mechanisms and Techniques in Photodynamic Therapy XI* (Proceedings of SPIE 2002) which is expressly incorporated by reference herein in its entirety. In this regard, the use of liposomes etc., as delivery vehicles for compounds of the invention would be desired. For example, a compound of the invention may be partially or totally encapsulated in a liposome or other microparticle. E may be hydrogen or a targeting moiety as previously described. The encapsulated compound may be administered to a patient whereby it may localize at an infected site. A photochemical procedure performed to detect the compound at the infected site and subsequently treat the infected area by activating the compound to kill the infectious agent.

Example 1 illustrates a specific embodiment of the invention pertaining to the preparation and properties of a compound of the invention derived from bombesin (a bioactive peptide) and a photochemical compound. Examples 2-6 illustrate the preparation of specific embodiments of the invention.

EXAMPLE 1

Synthesis of Photochemical Compound-Bombesin (7-14) Conjugate

The peptide is prepared by fluorenylmethoxycarbonyl (Fmoc) solid phase peptide synthesis strategy with a commercial peptide synthesizer from Applied Biosystems (Model 432A SYNERGY Peptide Synthesizer). The first peptide cartridge contains Wang resin pre-loaded with an amide resin on 25-mole scale. The amino acid cartridges are placed on the peptide synthesizer, and the product is synthesized from the C- to the N-terminal position. Coupling of the Fmoc-protected amino acids (75 µmol) to the resin-bound free terminal amine (25 µmol) is carried out with 2-(1H-benzotriazol-1-yl)-1,1,3,3-tetramethyluronium hexafluorophosphate (HBTU, 75 µmol)/N-hydroxybenzotriazole (HOBt, 75 µmol). Each Fmoc protecting group on solid support is removed with 20% piperidine in dimethylformamide before the subsequent amino acid is coupled to it. The last cartridge contains the Ar-PA compound, which is coupled to the peptide automatically, thus avoiding the need for post-synthetic manipulations.

After the synthesis is completed, the product is cleaved from the solid support with a cleavage mixture containing trifluoroacetic acid (85%):water (5%):phenol (5%):thioanisole (5%) for six hours. The peptide-photosensitizer/photoactive compound conjugate is precipitated with t-butyl methyl ether and lyophilized in water:acetonitrile (2:3) mixture. The conjugate is purified by HPLC and analyzed with LC/MS.

EXAMPLE 2

Preparation of 3-[3,6-diamino-5-(2-methoxyethylcarbamoyl)pyrazine-2-carboxamido]propanoic acid (1)

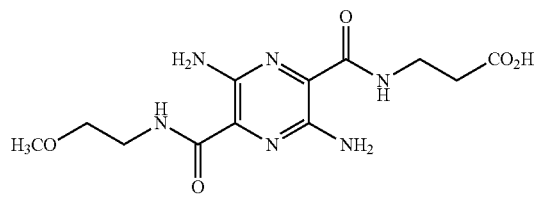

1

Step 1. To a suspension of the diacid 7 (FIG. 1) (201 mg) in dry DMF (20 mL) was treated with 2-methoxyethylamine (92

μL) and stirred under argon atmosphere for 15 minutes. Thereafter, β-alanine benzyl ester (374 mg) and Hunig base (N,N-diisopropylethylamine) (186 μL) were added and the entire mixture was stirred for additional 45 minutes. Finally, 1-hydroxybenzotriazole monohydrate (288 mg) and EDC hydrochloride (211 mg) were added and the mixture stirred under argon atmosphere at ambient temperature of about 16 hours. The solvent was removed under reduced pressure and the residue was dissolved in ethyl acetate (20 mL). The solution was washed with water and brine, dried over sodium sulfate, filtered, and the filtrate evaporated in vacuo. The crude product was purified by column chromatography over silica gel using methylene chloride/ethyl acetate as eluent to furnish 100 mg of the desired benzyl ester 13. NMR and LC/MS were consistent with the structure.

Step 2. A solution the benzyl ester 13 (480 mg) in methanol (20 mL) was treated with Pd—C (10%) (50 mg) and hydrogenated at 14 psi (1 atm) for 2 hours. TLC indicated completion of the reaction. The solution was filtered over Celite and the filtrate evaporated in vacuo to give 206 mg of the desired acid 1. NMR and LC/MS were consistent with the structure.

EXAMPLE 3

Preparation of 3,6-diamino-$N^2$-2-(aminoethyl)-$N^5$-2-(methoxyethyl)pyrazine-2,5-dicarboxamide (2)

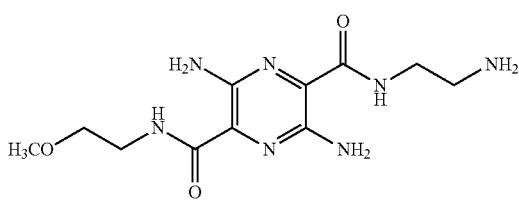

2

Step 1. To a suspension of the diacid 7 (FIG. 1) (1.00 g) in dry DMF (25 mL) was treated with 2-methoxyethylamine (92 μL) and Boc-ethylenediamine (1.12 mL). The mixture was stirred under argon atmosphere for 5 minutes. The mixture was then cooled in ice-bath and treated with 1-hydroxybenzotriazole monohydrate (1.91 g) added in two portions over a 20-minute period. Thereafter, EDC hydrochloride (2.71 g) was added and the mixture stirred under argon atmosphere at ambient temperature of about 18 hours. LC/MS indicated that the reaction was complete. The solvent was removed under reduced pressure and the residue was dissolved in chloroform (250 mL). The solution was washed with water, saturated sodium bicarbonate, and brine, dried over sodium sulfate, filtered, and the filtrate evaporated in vacuo. The crude product was purified by column chromatography over silica gel using chloroform/methanol as eluent to furnish 500 mg of the desired Boc-protected intermediate 11. NMR and LC/MS were consistent with the structure.

Step 2. A solution the Boc derivative 11 (500 mg) in methylene chloride (20 mL) was treated with trifluoroacetic acid (TFA) (6 mL) and kept at ambient temperature for 2 hours. LC/MS indicated completion of the reaction. The solvent and excess TFA evaporated in vacuo to give 900 mg of the desired acid amine 2 as the bis-TFA salt. NMR and LC/MS were consistent with the structure.

EXAMPLE 4

Preparation of 3,6-Bis(N-propylamino)-$N^2$-2-(aminoethyl)-$N^5$-2-(methoxyethyl)pyrazine-2,5-dicarboxamide (3)

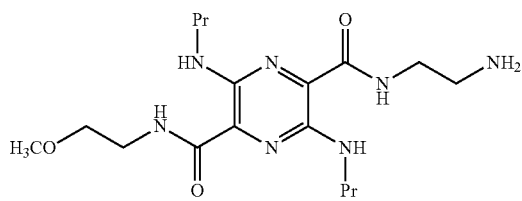

3

Step 1. A solution the Boc derivative 11 in Example 2 (1.5 g) in dichloroethane (30 mL) was treated with propionaldehyde (1.1 mL) and cooled to 0° C. Thereafter, glacial acetic acid (0.86 mL) was added and the mixture stirred at 0° C. for 15 minutes. Sodium triacetoxyborohydride (3.2 g) was added in 4 portions, and the entire mixture was stirred at ambient temperature for 24 hours. The reaction mixture was carefully quenched with saturated sodium bicarbonate solution (25 mL). The organic layer was separated, washed with water, dried over sodium sulfate, filtered, and the filtrate evaporated in vacuo. The crude product was purified by flash chromatography over silica gel using chloroform/methanol (0 to 1%) as gradient to furnish 670 mg of the desired Boc-protected intermediate. NMR and LC/MS were consistent with the structure.

Step 2. A solution the Boc derivative above (620 mg) in methylene chloride (20 mL) was treated with trifluoroacetic acid (TFA) (6 mL) and kept at ambient temperature for 3 hours. LC/MS indicated completion of the reaction. The solvent and excess TFA evaporated in vacuo to give 1.1 g of the desired acid amine 3 as the bis-TFA salt. NMR and LC/MS were consistent with the structure.

EXAMPLE 5

Preparation of 3,6-Bis(N-propylamino)-$N^2,N^5$2-bis(2-aminoethyl)-2,5-dicarboxamide (4)

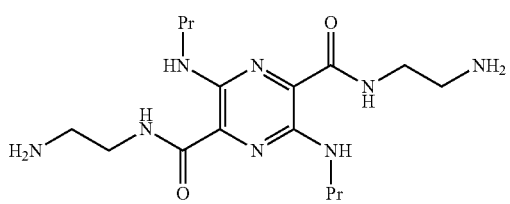

4

Step 1. A mixture of the diacid 7 (1.0 g) and Boc-ethylenediamine (2.4 g) in dry DMF (25 mL) was stirred at ambient temperature for 30 minutes. Thereafter, 1-hydroxybenzotriazole monohydrate (1.75 g) and EDC hydrochloride (2.74 g) were added and the mixture stirred at ambient temperature for about 3 days. The reaction mixture was poured onto ether (200 mL) and the precipitate was allowed to settle at the bottom of the flask. Excess ether and DMF were decanted off and the precipitate resuspended in ether and stirred. Excess ether again decanted off and the process repeated two more times. The dark brown gummy residue was treated with water (100 mL). The greenish-yellow precipitate was collected by filtration, washed well with water, and dried to give the desired bis-Boc intermediate. NMR and LC/MS were consistent with the structure.

Step 2. A solution the bio-Boc derivative in Step 1 (0.97 g) in dichloroethane (40 mL) was treated with propionaldehyde (0.6 mL) and cooled to 0° C. Thereafter, glacial acetic acid (0.46 mL) was added and the mixture stirred at 0° C. for 10 minutes. Sodium triacetoxyborohydride (1.7 g) was added in 6 portions over 15 minutes, and the entire mixture was stirred at ambient temperature for 24 hours. The reaction mixture was carefully quenched with saturated sodium bicarbonate solution (30 mL). The organic layer was separated, washed with water, dried over sodium sulfate, filtered, and the filtrate evaporated in vacuo. The crude product was purified by flash chromatography over silica gel using chloroform/methanol (0 to 1%) as gradient to furnish 1.1 g of the desired N,N'-dialkylated Boc-protected intermediate. NMR and LC/MS were consistent with the structure.

Step 3. A solution the Boc derivative above (1.1 g) in methylene chloride (15 mL) was treated with trifluoroacetic acid (TFA) (15 mL) and kept at ambient temperature for 3 hours. LC/MS indicated completion of the reaction. The solvent and excess TFA evaporated in vacuo to give 1.8 g of the desired acid amine 4 as the bis-TFA salt. NMR and LC/MS were consistent with the structure.

EXAMPLE 6

Preparation of 3,6-diamino-$N^2$-6-(3-aza-4-oxa-6-maleimidohexyl)amino-$N^5$-2-(methoxyethyl)pyrazine-2,5-dicarboxamide (5)

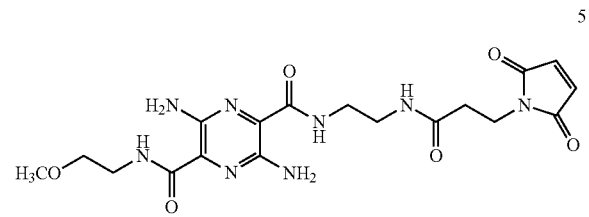 [SMILES: COCCNC(=O)c1nc(N)c(C(=O)NCCNC(=O)CCN2C(=O)C=CC2=O)nc1N]

A mixture of compound 2 in Example 2 (73 mg) in DMF (1 mL) was cooled to 0° C. and treated with Hunig base (120 μL). After stirring for about 30 minutes, maleimidopropionic acid N-succinimo ester (27 mg) was added, and the entire mixture stirred at ambient temperature for 16 hours. Excess solvent was removed by evaporation under reduced pressure and residue was dissolved in chloroform (10 mL). The solution was washed with 0.1 M KHSO4, saturated sodium bicarbonate, and brine. The organic layer was dried over sodium sulfate, filtered, and the filtrate evaporated in vacuo. The crude material was purified by automated flash chromatography using chloroform/methanol gradient to give 29 mg of the desired product 5 as yellow powder. NMR and LC/MS were consistent with the structure.

REFERENCES

1. Hassan, M.; Klaunberg, B. A. Biomedical applications of fluorescence imaging in vivo. *Comparative Medicine* 2004, 54 (6), 635-644.
2. Licha, K.; Olbrich, C. Optical imaging in drug discovery and diagnostic applications. *Advances in Drug Delivery Reviews* 2005, 57 (8), 1087-1108.
3. Shah, K.; Weissleder, R. Molecular optical imaging: applications leading to the development of present day therapeutics. *NeuroRx* 2005, 2 (2), 215-225.
4. Solban N.; Ortel, B.; Pogue, B.; Hasan, T. Targeted optical imaging and photodynamic therapy. *Ernst Schering Research Foundation Workshop* 2005, 49, 229-258.
5. Jain, R. K. Barriers to Drug Delivery in Solid Tumors. *Scientific American* 1994, 271, 58-65.
6. Shirai, K. et al. Synthesis and fluorescent properties of 2,5-diamino-3,6-dicyanopyrazine dyes. *Dyes and Pigments* 1998, 39, 49-68.
7. Kim, J. H, et al. Self-assembling of aminopyrazine fluorescent dyes and their solid state spectra. *Dyes and Pigments* 1998, 39, 341-357.
8. Hemnanson, G. T. *Bioconjugate Techniques*, 2$^{nd}$ Edition. Academic Press: New York, 2008.
9. Achilefu et al., Novel receptor-targeted fluorescent contrast agents for in vivo imaging of tumors, *Investigative Radiology*, 2000, 35, 479-485.
10. Ballou et al., Tumor labeling in vivo using cyanine conjugated monoclonal antibodies, *Cancer Immunology and Immunotherapy*. 1995, 41, 257-263.
11. Licha et al., New contrast agent for optical imaging: acid cleavable conjugates of cyanine dyes with biomolecules, in *Biomedical Imaging: Reporters, Dyes and Instrumentation*, Proceedings of SPIE, 1999, 3600, 29-35.

It should be understood that the embodiments of the present invention shown and described in the specification are only exemplary embodiments of the invention and are not limiting in any way. As known to one skilled in the art, various changes and modifications are possible and are contemplated within the scope of the invention described. For example, compounds containing polycyclic aromatic photosensitizers may also be used in optical diagnostic imaging. Therefore, various changes, modifications or alterations to those embodiments may be made or resorted to without departing from the spirit of the invention and the scope of the following claims.

What is claimed is:
1. A compound of the formula: E1-L-Ar—X-PA (Formula IX), wherein:
Ar is

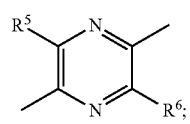

Formula 1

E1 is hydrogen;
X is selected from a single bond, —$(CH_2)_a$—, —CO—, —OCO—, —HNCO—, —$(CH_2)_a$CO—, —$(CH_2)_a$OCO—, C5-C10 aryl, C5-C10 heteroaryl, —$NR^1$CO—, —$(CH_2)_a CONR^1$—, —$(CH_2)_a$SO—, —$(CH_2)_a$CON($R^1$)—, —$(CH_2)_a N(R^1)$CO—, —$(CH_2)_a N(R^1)$CON($R^2$)— and —$(CH_2)_a N(R^1)$CSN($R^2$)—, —CON($R^1$)$(CH_2)_a$—;
L is selected from a single bond, —HNCO—, —$CONR^3$, —$(CH_2)_b$—, —$(CH_2)_b CONR^3$—, —$N(R^3)$CO$(CH_2)_b$—, —OCO$(CH_2)_b$—, —$(CH_2)_b CO_2$—, —OCONH—, —$OCO_2$—, —HNCONH—, —HNCSNH—, —HNNHCO—, —$OSO_2$—, —$NR^3(CH_2)_b$ $CONR^4$—, —$CONR^3(CH_2)_bNR^4CO$—, —$NR^3CO$
$(CH_2)_bCONR^4$—, —$(CH_2)_bCON(R^3)$—, —$(CH_2)_bN(R^3)CO$—, —$(CH_2)_bN(R^3)CON(R^4)$— and —$(CH_2)_bN(R^3)CSN(R^4)$—;

PA is —OZ or —$NR^9Z$;

Z is selected from —$(CH_2)_cCO_2H$, —$(CH_2)_cNR^9R^{10}$, —$(CH_2)_cNCO$, —$(CH_2)_cNCS$, —$(CH_2)_cSH$, —$(CH_2)_cC\equiv CH$, —$(CH_2)_cC\equiv N$, —$(CH_2)_cN_3$,

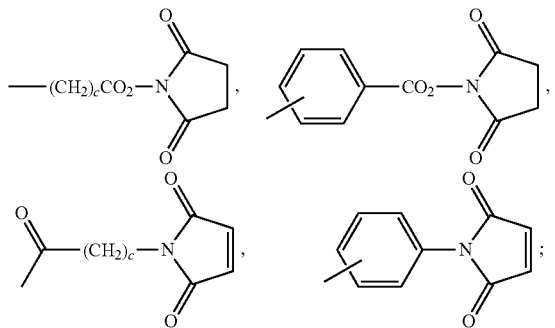

each $R^1$, $R^2$, $R^3$, and $R^4$ is independently selected from hydrogen, C1-C10 alkyl, —OH, C5-C10 aryl, C1-C10 hydroxyalkyl, C1-C10 polyhydroxyalkyl, C1-C10 alkoxyl, C1-C10 alkoxyalkyl, —$(CH_2)_cCO_2H$, and —$(CH_2)_cNR^9R^{10}$;

$R^5$ and $R^6$ are each independently —$(CH_2)_fNR^{16}R^{17}$;

$R^9$ and $R^{10}$ are each independently selected from hydrogen, C1-C10 alkyl, C5-C10 aryl, and C1-C10 maleimidoalkylcarbonyl;

$R^{16}$ and $R^{17}$ are each independently hydrogen, $C_1$-$C_{10}$ alkyl, C5-C10 aryl, $C_1$-$C_{10}$ hydroxyalkyl, and $C_1$-$C_{10}$ alkoxyalkyl;

each a is an integer independently selected from 0 to 10;
each b is an integer independently selected from 0 to 10;
each c is an integer independently selected from 0 to 10; and
each f is an integer independently selected from 0 to 10.

2. The compound of claim 1, wherein f is 0.

3. The compound of claim 1 wherein PA is —$NR^9Z$.

4. The compound of claim 3 wherein $R^{16}$ is hydrogen or C1-C10 alkyl.

5. The compound of claim 1 wherein L is —$CONR^3$— and $R^3$ is C1-C10 alkoxyalkyl, —$(CH_2)_cCO_2H$, or —$(CH_2)_cNR^9R^{10}$.

6. The compound of claim 5 wherein $R^3$ is C1-C10 alkoxyalkyl.

7. The compound of claim 1 wherein Z is

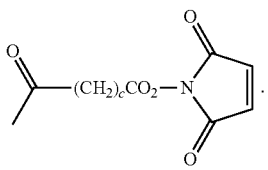

8. The compound of claim 1 wherein Z is

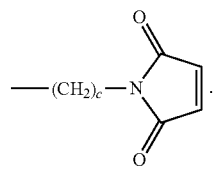

9. The compound of claim 1 wherein Z is —$(CH_2)_cCO_2H$.

10. The compound of claim 1 wherein $R^3$ is —$(CH_2)_cNR^9R^{10}$.

11. The compound of claim 1 wherein Z is —$(CH_2)_cNR^9R^{10}$.

12. The compound of claim 11 wherein $R^9$ and $R_{10}$ are both hydrogen.

13. The compound of claim 1, wherein Z is selected from:

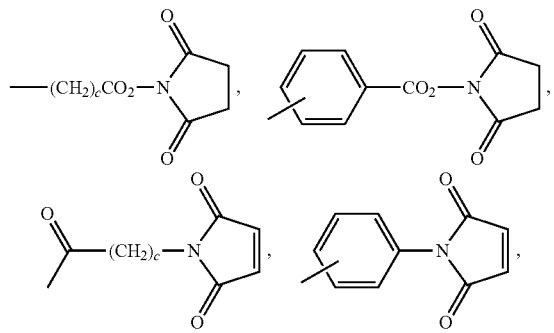

or —$(CH_2)_cNR^9R^{10}$ where $R^9$ or $R^{10}$ is C1-C10 maleimidoalkylcarbonyl.

14. The compound of claim 1, wherein:
E1 is hydrogen;
X is —$CON(R^1)(CH_2)_a$—;
L is —$CONR^3$—;
PA is —OZ or —NHZ;
Z is selected from the group consisting of —$(CH_2)_cCO_2H$, —$(CH_2)_cNR^9R^{10}$, —$(CH_2)_cNCO$, —$(CH_2)_cNCS$, —$(CH_2)_cSH$, —$(CH_2)_cC\equiv CH$, —$(CH_2)_cC\equiv N$, —$(CH_2)_cN_3$,

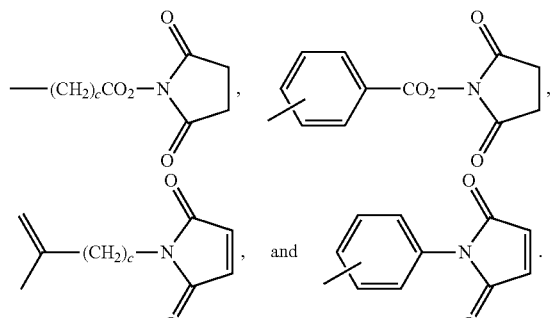

$R^3$ is selected from the group consisting of hydrogen, C1-C10 alkyl, —OH, C5-C10 aryl, C1-C10 hydroxyalkyl, C1-C10 polyhydroxyalkyl, C1-C10 alkoxyl, C1-C10 alkoxyalkyl, —$(CH_2)_cCO_2H$, and —$(CH_2)_cNR^9R^{10}$;

$R^5$ and $R^6$ are each independently —$(CH_2)_fNR^{16}R^{17}$;

$R^9$ and $R^{10}$ are each independently selected from the group consisting of hydrogen, C1-C10 alkyl, C5-C10 aryl, and C1-C10 maleimidoalkylcarbonyl;

$R^{16}$ and $R^{17}$ are each independently selected from the group consisting of hydrogen, C1-C10 alkyl, C5-C10 aryl, C1-C10 hydroxyalkyl, and C1-C10 alkoxyalkyl;

each c is an integer independently selected from 0 to 10; and f is 0.

* * * * *